US012582612B2

(12) United States Patent
Wu et al.

(10) Patent No.: US 12,582,612 B2
(45) Date of Patent: Mar. 24, 2026

(54) PHARMACEUTICAL COMPOSITION OF SIGLEC-BINDING AGENTS

(71) Applicant: CYTODIGM, INC., Natick, MA (US)

(72) Inventors: Bin Wu, Lexington, MA (US); Zimeng Wang, Framingham, MA (US); Nicholas Boylan, Boylston, MA (US); Jieni Xu, Quincy, MA (US)

(73) Assignee: Cytodigm, Inc., Natick, MA (US)

( * ) Notice: Subject to any disclaimer, the term of this patent is extended or adjusted under 35 U.S.C. 154(b) by 0 days.

(21) Appl. No.: 17/494,555

(22) Filed: Oct. 5, 2021

(65) Prior Publication Data

US 2022/0142935 A1 May 12, 2022

Related U.S. Application Data

(60) Provisional application No. 63/087,454, filed on Oct. 5, 2020.

(51) Int. Cl.
*A61K 9/51* (2006.01)
*A61K 45/06* (2006.01)

(52) U.S. Cl.
CPC .......... *A61K 9/5161* (2013.01); *A61K 9/5123* (2013.01); *A61K 9/5192* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 2008/0213349 | A1 | 9/2008 | Thakker et al. | |
| 2009/0148384 | A1 | 6/2009 | Fischer et al. | |
| 2013/0058998 | A1 | 3/2013 | Huizing et al. | |
| 2013/0324592 | A1 | 12/2013 | Rodriguez et al. | |
| 2019/0269635 | A1 * | 9/2019 | Nikoulin .................. | A61K 9/10 |
| 2021/0169819 | A1 | 6/2021 | Wu | |

FOREIGN PATENT DOCUMENTS

| | | | |
|---|---|---|---|
| EP | 2100597 | A2 | 9/2009 |
| ES | 2341165 | A1 | 6/2010 |
| WO | 2015160597 | A1 | 10/2015 |
| WO | 2019158060 | A1 | 8/2019 |

OTHER PUBLICATIONS

Kim, Y-H., et al., "Development of Sialic Acid-coated Nanoparticles for Targeting Cancer and Efficient Evasion of the Immune System", Theranostics, 7(4), 2017, 962-973.

* cited by examiner

*Primary Examiner* — Bong-Sook Baek
(74) *Attorney, Agent, or Firm* — Elmore Patent Law Group, P.C.; Jia Kang; Carolyn S. Elmore

(57) ABSTRACT

This invention provides a pharmaceutical composition comprising an agent that can bind Siglec receptors on cell surface. This invention also provides the method of preparing said pharmaceutical composition and the use thereof.

13 Claims, 14 Drawing Sheets

In vitro blood 4 h

PLGA 10 ug/mL (4 hour)
Zetafinity 10 ug/mL (4 hour)
Signifity 10 ug/mL (4 hour)

In Vitro Blood 4h 10 mg/ml

% DiD+ cells

NK
DC
Monocytes
Macrophages
B cells
CD8
CD4

PLGA 50 ug/mL (4 hour)
Zetafinity 50 ug/mL (4 hour)
Signifity 50 ug/mL (4 hour)

In Vitro Blood 4h 50 mg/ml

% DiD+ cells

NK
DC
Monocytes
Macrophages
B cells
CD8
CD4

In vivo spleen-Zetafinity

In Vivo 4h Spleen DiD+ Monocytes
% Ly6-C+
CD45+CD3-F4/80+CD11b+CD11c-Ly6-C+DiD+

In Vivo 4h Spleen Monocytes
% CD11b+CD11c-
CD45+CD3-F4/80+CD11b+CD11c-Ly6-C+

In Vivo 4h Spleen DiD+ B Cells
% CD20+
CD45+CD3-CD20+DiD+

In Vivo 4h Spleen B Cells
% CD3-
CD45+CD3-CD20+

In Vivo 4h Spleen DiD+ T Cells
% CD3+
CD45+CD3+DiD+

In Vivo 4h Spleen T Cells
% CD45+
CD45+CD3+

PHARMACEUTICAL COMPOSITION OF SIGLEC-BINDING AGENTS

RELATED APPLICATION

This application claims the benefit of U.S. Provisional Application No. 63/087,454, filed on Oct. 5, 2020. The entire teachings of the above application are incorporated herein by reference.

BACKGROUND OF THE INVENTION

Many therapeutic agents need to be delivered to certain targets in the human body. Such target can be an organ, a certain type of tissue, or a specific receptor on a type of cell. In some cases, it is desirable to deliver a therapeutic agent to a specific type of cell so that the therapeutic agent binds a certain receptor on the cell surface, and such binding can lead to desirable immunological or biological effects. In other cases, it may be desirable to deliver a therapeutic agent into a certain type of cell. Due to the lack of targeting many drugs could not fully realize their optimal therapeutic potential and even cause adverse effects. For example, only a small fraction of chemotherapeutic agents administered orally or systemically reaches tumor sites.

Siglec, sialic acid-binding immunoglobulin-like lectin, is an immunosuppressive carbohydrate-recognition receptor. Most Siglecs are expressed by various immune cells and have an intracellular immunoreceptor tyrosine-based inhibition motif (ITIM) that upon binding to sialic acid can activate downstream inhibitory signaling through the recruitment of tyrosine phosphatases SHP-1 and SHP-2. A smaller group of Siglecs have an intracellular immunoreceptor tyrosine-based activation motif (ITAM) that upon binding to sialic acid can activate downstream stimulatory signaling.

Sialic acid is a nine-carbon sugar that binds to Sialic acid, also known as N-acetylneuraminic acid, is a significant regulator of phagocytic evasion. Sialic acid has mainly three derivatives, N-acetyl neuraminic acid (Neu5Ac), N-acetyl neuraminic acid hydroxyalkyl (Neu5Gc) and 3-deoxy-D-glycero-D-galacto-nonyl ketose (Kdn). There are other sialic acid derivatives that are further derived from these primary derivatives. One important sialic acid derivative is ganglioside, which is found in the brain. Sialic acid can also regulate the alternative pathway of complement activation. Major serum protein complement factor H recognizes sialic acid as a "self" marker, which helps to inhibit C1q/C3b fragment activation. In addition, sialic acid also binds a carbohydrate-binding lectin overexpressed in several types of cancers.

Aberrant interactions between sialic acid and Siglec are associated with a number of pathologies including infection, autoimmunity, and cancer. It can therefore be therapeutically beneficial to bind Siglecs on certain types of cells with ligands that contain sialic acid moiety to modulate the immune inhibition or activation for the treatment of pathologies including infection, autoimmunity, and cancer. However, it is challenging to use sialic acid or sialic acid containing glycans to directly target Siglec receptors on the surface of cells in vivo.

One strategy for binding cell receptors is to use an antibody that is designed to bind the specific receptor of target. In that case, the antibody itself is the therapeutic agent. For example, CD22, also known as Siglec-2, is an inhibitory co-receptor of the B-cell receptor (BCR) on B cells and plays a crucial role in activation and differentiation of the B cells (Nischke, L. et al, CD22 and Siglec-G: B-cell inhibitory receptors with distinct functions. Immunol. Rev. 2009, 230: 128-143). Epratuzumab, a humanized monoclonal antibody of CD22, showed promising result in clinical trials with systemic lupus erythematosus (SLE) by modulating BCR signaling like calcium mobilization and phosphorylation of downstream signaling molecules (Clowse M E, et al., Efficacy and Safety of Epratuzumab in Moderately to Severely Active Systemic Lupus Erythematosus: Results From Two Phase III Randomized, Double-Blind, Placebo-Controlled Trials, Arthritis Rheumatol Actions. 2017 February; 69(2):362-375).

Antibody can also be used to carry a therapeutic agent into the cell via receptor-mediated endocytosis. For example, a drug molecule can be conjugated to an antibody which guides the drug to the cell followed by antibody binding the cell receptor and drug being internalized by the cell. A drug can also be encapsulated into a nanoparticle and an antibody is then conjugated to said drug-loaded nanoparticle. Thus, the antibody guides the nanoparticle to the cell of targeting.

There has been some success in using such antibody strategy to deliver drugs to the targeted sites. However, this approach has disadvantages. For example, antibodies are prone to hydrolysis and degradation in the body fluid and as a result, a significant portion of the antibody administered may lose its activity due to the hydrolysis and degradation. In addition, developing and producing antibodies are costly.

In summary, there are unmet needs in the field of treating infection, autoimmunity, and cancer for 1) developing a pharmaceutical composition that is capable of delivering Siglec-binding ligands to bind specific Siglecs on cell surface to regulate downstream immune responses and 2) developing a pharmaceutical composition that is capable of delivering therapeutic agents to certain cells via receptor-mediated endocytosis by targeting Siglecs on cell surface.

SUMMARY OF THE INVENTION

The present invention provides a pharmaceutical composition capable of binding Siglec receptors on cell surface, wherein said composition comprises a non-covalent complex formed by a Siglec-binding agent and a counterion thereof. Siglec-binding agents can be selected from the group consisting of sialic acid, sialic acid derivatives, mimetics and other entities that contain sialic acid moiety in their chemical structure, herein collectively referred to as sialic acid (SA)-containing entity. The pharmaceutical composition can be formed by forming a non-covalent complex between the SA-containing agent and one of its counterions, wherein said non-covalent complex may be a soluble entity or an insoluble particle. It is preferred that the non-covalent complex is an insoluble particle (e.g. a nanoparticle) that forms stable suspension in an aqueous solution. The SA-containing agent can be a polysialic acid.

The present invention provides compositions comprising nanoparticles comprising a polysialic acid or polymer co-precipitated with a counterion complexing agent, wherein said complexing agent can be a small-molecule complexing agent, a cationic lipid, an ionizable lipid, a cationic polymer or an ionizable polymer, and an optional active pharmaceutical ingredient.

The polysialic acid is preferably water-soluble. The polysialic acid can comprise a plurality of sialic acid residues selected from the group consisting of Neu5Ac, Neu5Gc, and Kdn, or a combination thereof. The polysialic acid can have a molecular weight of from 500 to 50,000,000, from 1,000 to 5,000,000, and from 2,000 to 500,000 Da.

In some embodiments, the polysialic acid is a polysialic acid comprising only sialic acid repeating units. This type of polymer is often referred as a "homopolymer." One example of such homopolymer of polysialic acid is colominic acid, commercially available, for example, from Carbosynth, Oakbrook Terrace, IL, USA. Colominic acid, also referred to as polysialic acid, is a linear small polysaccharide containing α-2,8-linked sialic acid (neuraminic acid) with (n=8 to >100) residues. The sialic acid unit in the SA-containing agent or polysialic acid has an alpha-2,3 linkage, an alpha-2,6 linkage or an alpha-2,8 linkage or combinations thereof.

In some embodiments, the polysialic acid is a "copolymer" comprising sialic acid repeating units and the repeating units of at least one different chemical entity. Non-limiting examples of such copolymers include PLGA-PSia, PEG-PSia, PLGA-PEG-PSia, etc. Here, PLGA is poly(lactide-co-glycolide), PEG is polyethylene glycol and PSia is polysialic acid.

In some embodiments, the polysialic acid is an oligomer of sialic acid, such as a dimer, a trimer, a tetramer, a pentamer or a hexamer available as N-acetylneuraminic acid oligomers or their sodium salts, available from Nacalai USA, Inc., San Diego, CA, United States.

In some embodiments, the polysialic acid is a pharmaceutically acceptable polymer having a sialic acid moiety at the terminal of its chemical structure. For example, PEG-Sia, or PLGA-PEG-Sia, where Sia represents the sialic acid moiety.

Preferably, the polysialic acid can be a homopolymer or colominic acid.

Preferably, a complexing agent can be added to the SA-agent to co-precipitate to form said nanoparticle formulation. The complexing agent may be neutral, anionic or cationic. A cationic complexing agent is preferred in the present invention. A cationic complexing agent may be a nitrogen, sulfur or phosphorus containing molecule such as a small molecule compound, a lipid, a polymer or a dendrimer. The molecule is preferably amphiphilic, having one or more cationic moieties and one or more hydrophobic moieties. Cationic moieties can be nitrogen, sulfur or phosphorus containing groups. Preferred cationic moieties include primary or secondary amines, ammoniums or phosphoniums. The hydrophobic moiety can be an organic or inorganic group. Preferred hydrophobic groups include substituted or unsubstituted, saturated or unsaturated higher alkyls, acyls or esters (C3-C20 or more). The hydrophobic groups can be linear, branched or cyclized (such as aryl groups or cholesterol and analogs thereof).

Small molecule complexing agent used in the present invention is typically a nitrogen, sulfur or phosphorus containing compound or salt thereof. Non-limiting examples of small molecule complexing agents include ethyl lauroyl arginate HCl (LAE), tripropyl amine, tributyl amine, triphenyl amine, hexadecylamine, hexylamine, Didodecyldimethylammonium bromide, Dodecyltrimethylammonium bromide (DTAB), Cetrimonium bromide (CTAB), benzathine, dimethyldioctadecylammonium bromide, benethamine, hydrabamine, stearalkonium chloride, DC-Cholesterol.HCl, cetylpyridinium chloride, 1,2-distearoyl-3-dimethylammonium-propane, DODMA, lipofectin, etc.

The cationic lipid is typically pharmaceutically acceptable and can be a natural or synthetic lipid. An example of a cationic lipid is an ammonium lipid, or lipid characterized by a positively charged nitrogen moiety. For example, the cationic lipid can be substituted by a tertiary ammonium group, such as a trialkyl ammonium, preferably a trimethyl ammonium. The cationic lipid can be further substituted by one or more substituted or unsubstituted long chain alkyls or alkenyls, such as a G4-C20 alkyl or alkenyl. Examples of commonly used lipids include multivalent cationic lipid, DOTMA, ethyl PC's, DDAB, pH sensitive lipids, dioleoyl-3-trimethylammonium propane (DOTAP), DC-cholesterol, GL67, and DODMA.

An ionizable lipid is a class of lipid molecules that are neutral and non-ionic at physiological pH, but will be protonated to become positively charged at lower pHs. Ionizable lipids can also form the complex with the SA-containing entity while promoting endosome escape and reducing toxicity. Examples of commercially available ionizable lipids include DLin-KC2-DMA, DLin-MC3-DMA, DLin-DMA, DODMA, and DODAP.

In order to increase the stability, functionality and other performance properties of the complex nanoparticles, other chemical entities commonly used in lipid nanoparticle (LNP) formulations such as structural lipids, PEGylated lipids, cholesterol, phospholipids, etc. may be added to the nanoparticle formulations of the present invention.

The complexing agent can also be a cationic polymer or an ionizable polymer.

A cationic or ionizable polymer can be of natural or synthetic origin. Natural cationic or ionizable polymer can be a protein such as gelatin, or a polysaccharide such as cationic chitosan, cellulose and dextran. Examples of synthetic cationic polymers include poly(2-N,N'-dimethylaminoethylmethacrylate), polylysine, polyethyleneimine, poly (amidoamine)s, poly(amino ester)s, and poly(amino acid)s.

The nanoparticles preferably encapsulate an active pharmaceutical agent (or API), such as an anti-cancer agent or immunotherapeutic agent, within the particles. Alternatively or additionally, the API is covalently or ionically attached to the surface of the nanoparticles. For example, the API can be covalently attached to the particle surface via a hydrolysable bond that facilitates in vivo release.

The invention further provides for methods for delivering an active pharmaceutical ingredient to cells in a subject in need thereof. The invention comprises administering to the subject the composition. The nanoparticles are preferably administered to cells, such as T cells, B cells, macrophages, neutrophils, monocytes, dendritic cells, natural killer cells or microglia and combinations thereof.

The invention further relates to methods for the treatment of a disease or disorder, such as cancer or an autoimmune disease, in a subject in need thereof comprising administering to the subject the composition of the invention.

The invention also relates to methods for the preparation of nanoparticles. The method can comprise the steps of:

dissolving a polysialic acid and, optionally, a water soluble active pharmaceutical ingredient in an aqueous solvent to form an aqueous solution;

dissolving a cationic lipid or a cationic polymer and, optionally, a water insoluble active pharmaceutical ingredient in a water-miscible organic solvent to form an organic solution;

combining the aqueous solution and organic solution, thereby precipitating nanoparticles; and collecting the nanoparticles.

DETAILED DESCRIPTION OF THE INVENTION

Overview

Figure 1A:
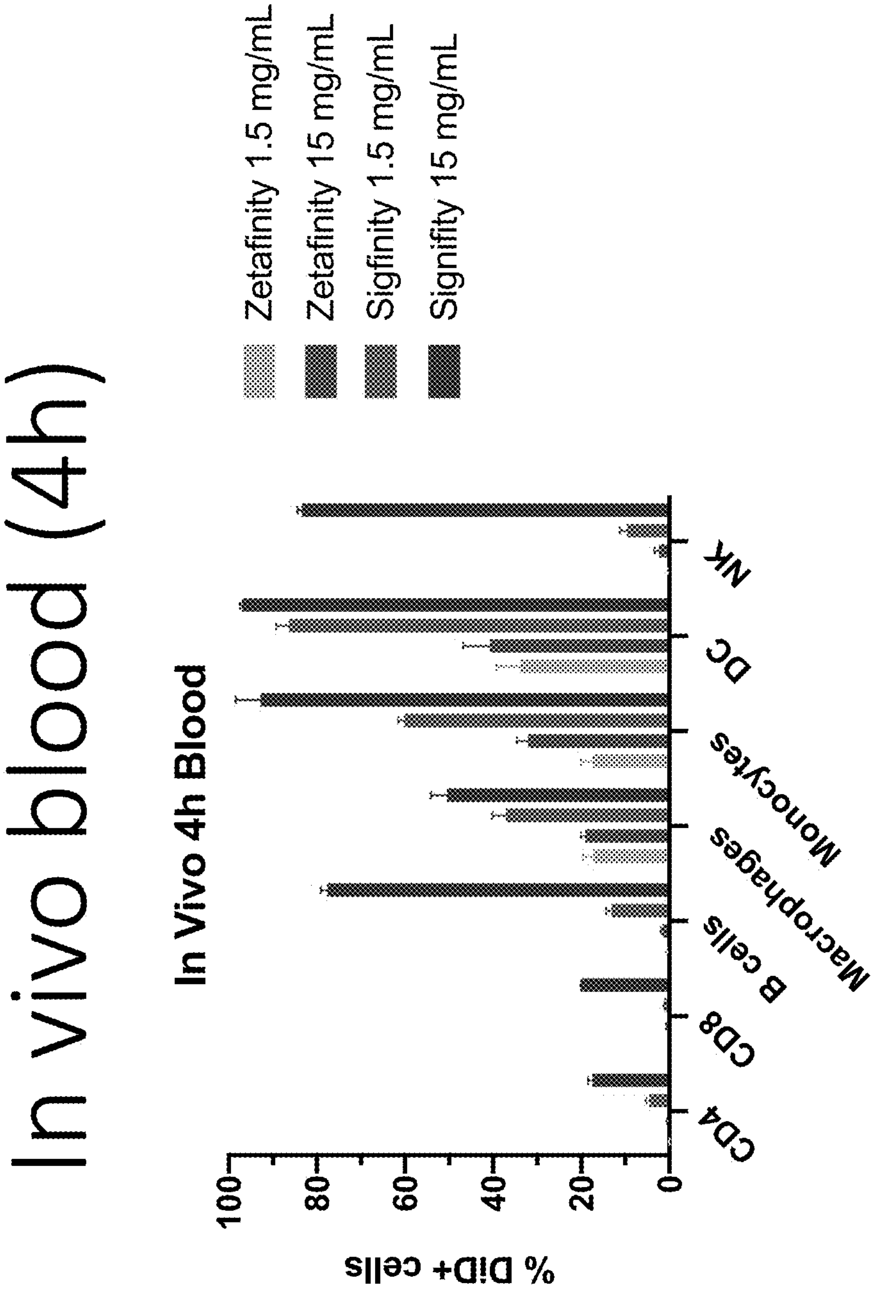
FIGS. 1A-1JJ illustrate particle uptake in the identified cell lines. The original figures are in color. In many figures, the bars moving from left to right along the x axis are identified by the legend moving from the top to the bottom.

Because aberrant interactions between sialic acid and Siglec are associated with a number of pathologies, including infection, autoimmunity, and cancer, providing particles presenting sialic acid moieties that bind Siglecs on certain cell can be therapeutically useful. The compositions comprising the particles can, for example, be used in the treatment of pathologies including infection, autoimmunity, and cancer. In addition, the interaction between sialic acid and Siglecs on specific immune cells can be used to guide particles comprising the sialic acid residues to the immune cells. Thus, particles that comprise a therapeutic agent as well as the sialic acid moieties can be targeted to specific immune cells.

The present invention provides nanoparticles that contain non-conjugated sialic acid residues, compositions, and methods of use thereof as well as non-conjugation methods to produce nanoparticles containing having sialic acid moieties. The non-conjugation methods described herein avoid the side reactions and side-products that have been observed when using conjugation methods to incorporate sialic acid residues.

The invention described herein provides pharmaceutical formulations comprising nanoparticles containing sialic acid residues (with or without agent/drug/API load), as well as processes capable of producing such pharmaceutical formulations comprising nanoparticles.

The invention includes methods for the preparation of that nanoparticles containing sialic acid residues, the methods comprising coprecipitation or coacervation of a polycation, such as a cationic lipid or polymer, and the polysialic acid. Using the methods of the invention, the polysialic acid is integrated into the produced nanoparticles.

With the invention generally described above, specific aspects of the invention are described further in the sections below.

Definitions

As used herein, "pharmaceutically acceptable" includes those compounds, materials, compositions, and/or dosage forms which are, within the scope of sound medical judgment, suitable for medical or veterinary use when in contact with the tissues of human beings and animals at the concentration, dosage or amount present in the product, without causing excessive toxicity, irritation, allergic response, or other problems or complications, commensurate with a reasonable benefit/risk ratio. Preferably, a pharmaceutically acceptable material (e.g., polymer, excipient, surfactant, solvent, or microparticles/nanoparticles produced therefrom) is suitable or approved for human medical use.

As used herein, "nanoparticles" are preferably roughly round, sphere, or sphere-like in shape, and are generally within the size range of, e.g., between about 1-1,000 nm, between about 10-1,000 nm, or between about 50-1,000 nm, or between about 100-500 nm, as measured by laser diffraction, for example. The subject nanoparticles may also include particles that are less likely to clump in vivo.

Particle size and size distribution can be measured by a dynamic light scattering instrument, e.g., a Malvern Zetasizer. The particle size is typically reported as a mass mean diameter. Alternative techniques include, for example, sedimentation field flow fractionation, photon correlation spectroscopy, light scattering, dynamic light scattering, light diffraction, and disk centrifugation. The term "nanoparticle" is not intended to convey any specific shape limitation. Such particles include, but are not limited to, those having a generally polyhedral or spherical geometry. Preferred particles are characterized by a spherical geometry typically produced by emulsion-based encapsulation processes. It is understood that the terms "microparticle" and "nanoparticle" are used interchangeably herein, unless accompanied by a specific description of size. For example, the term "microparticles" is intended to also embrace "nanoparticles" as if stated as "microparticles and/or nanoparticles" unless the context demands otherwise.

It is not necessary that each nanoparticle be uniform in size, although they are generally of a size sufficient to trigger phagocytosis in an antigen presenting cell (APC) or other MPS cell. Preferably, the subject nanoparticles have a diameter sufficient to trigger phagocytosis in an antigen presenting cell (APC) or other MPS cell.

The term "particle" encompasses both nanoparticle and microparticles.

As used herein "a" or "an" means one or more unless otherwise specified.

As used herein, "about" generally means up to ±10% of the particular term being modified.

A "polysialic acid" is a polymer comprising sialic acid monomers. Polysialic acids are described in more detail below.

The terms "sialic acid residue" and "sialic acid moiety" as well as their plural referents, and the like, are used interchangeably herein.

As used herein, the term "subject" is used to mean an animal, preferably a mammal, including a human or non-human. The terms "patient" and "subject" may be used herein interchangeably.

"Treatment" or "therapy" of a subject refers to any type of intervention or process performed on, or the administration of an active agent to, the subject with the objective of reversing, alleviating, ameliorating, inhibiting, slowing own or preventing the onset, progression, development, severity or recurrence of a symptom, complication, condition or biochemical indicia associated with a disease. As used herein, "treatment" (and grammatical variations thereof such as "treat" or "treating") includes to clinical intervention to alter the natural course of a disease in the individual being treated and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, combinations of the invention are used to delay development of a disease or to slow the progression of a disease.

Polysialic Acid

Polysialic acid (PSia) includes homopolymers of sialic acid. Naturally occurring PSia was first found in *E. coli* and is one of the ingredients of bacterial capsular materials, such as *Neisseria miningitidis* B, *Salmonella toucra* 048 and *Citrobacter freundii* 05. PSia can be in a conformation of α-2,8 (A in the figure below) or α-2,9 linkages (B in the figure below) or a mixture of α-2,8 and α-2,9. PSia constituted of α-2,8 bond is non-immunogenic and biodegradable and can reduce the immunogenicity of protein polypeptides. PSia possess the properties of escaping phagocytes and prolonging circulation time in vivo.

A

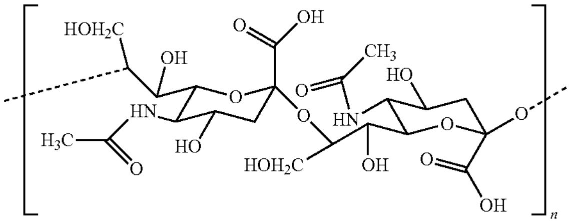

B

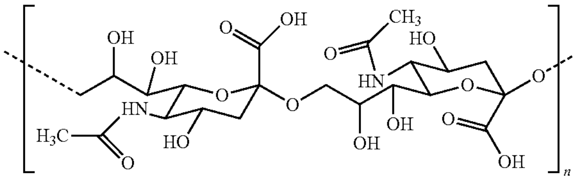

Therefore, nanoparticles having a sialic acid moiety may also facilitate RES escape and render the nanoparticles prolonged circulation in the bloodstream. In addition, since sialic acid also binds several receptors on tumor cells, sialic acid-coated nanoparticles can be leveraged to target tumor site via the high-avidity binding of sialic acid to lectins.

As described above, a polysialic acid is a polymer comprising a chain of sialic acid monomers. In certain aspects, the polymer is a homopolymer (e.g., all the sialic acid monomer units are the same). In other aspects, the polymer is a heteropolymer (e.g., the polysialic acid comprises at least two different sialic acid monomer units). In yet other aspects, the polymer comprises at least 5, at least 10, at least 15, at least 20, at least 30, at least 40, at least 50, at least 60, at least 75, at least 100, at least 200, or at least 300 sialic acid monomers. The sialic acid monomer can be any derivative of a neuraminic acid. Sialic acid monomers include, for example, N-acetylneuraminic acid (Neu5Ac), N-glycolylneuraminic acid (Neu5Gc), or deaminated neuraminic acid (Kdn; 3-deoxy-D-glycero-D-galactononulosonic acid. The sialic acid monomer is exemplified by Formula (I):

(I)

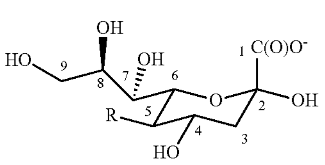

In Neu5Ac, R is —NH—C(O)—$CH_3$. In Neu5Gc, R is —NH—C(O)—$CH_2$—OH. In Kdn, R is OH. Other examples of sialic acid monomers are N-sialic acid, O-sialic acid, 9-O-acetyl-8-O-methyl-N-acetylneuraminic acid (Neu5,9Ac28Me), and 7,8,9-tri-O-acetyl-N-glycolylneuraminic acid (Neu5Gc7,8,9Ac3), Neu4,5Ac2; Neu5,7Ac2; Neu5,8Ac2; Neu5,9Ac2; Neu4,5,9Ac 3; Neu5,7,9Ac 3; Neu5,8,9Ac 3; Neu5,7,8,9Ac 4; Neu5Ac9Lt; Neu4,5Ac 29Lt; Neu5Ac8Me; Neu5,9Ac28Me; Neu5Ac8S; Neu5Ac9P; Neu2en5Ac; Neu2en5,9Ac 2; Neu2en5Ac9Lt; Neu2,7an5Ac; Neu5Gc; Neu4Ac5Gc; Neu7Ac5Gc; Neu8Ac5Gc; Neu9Ac5Gc; Neu7,9Ac 25Gc; Neu8,9Ac 25Gc; Neu7,8,9Ac 35Gc; Neu5Gc9Lt; Neu5Gc8Me; Neu9Ac5Gc8Me; Neu7,9Ac 25Gc8Me; Neu5Gc8S; Neu5GcAc; Neu5GcMe; Neu2en5Gc; Neu2en9Ac5Gc; Neu2en5Gc9Lt; Neu2en5Gc8Me; Neu2,7an5Gc; Neu2,7an5Gc8Me; and Knd9Ac.

As described above, sialic acid monomers can be joined by α-2,8-, α-2,9, or α-2,8/α-2-9-ketosidic linkages, for example. α-2,4-ketosidic linkages and α-2,5-ketosidic linkages have also been described (Janas et al. (2011), Biochimica et Biophysica Acta 1808: 2923-2932). The sialic acid monomers can be joined in any bonding arrangement. In certain embodiments, the polysialic acid comprises monomers that are 2→8 linked, 2→9 linked, or a combination thereof. In yet other aspects, the monomers are all 2→8 linked or all 2→9 linked. In further aspects, the polysialic acid comprises Neu5Ac monomers that are 2→8 linked, 2→9 linked, or a combination thereof. In yet other aspects, the polysialic acid comprises Neu5Gc monomers that are 248 linked, 2→9 linked, or a combination thereof. In further embodiments, the polysialic acid comprises Kdn monomers that are 2→8 linked, 2→9 linked, or a combination thereof. The polysialic acid can be a homopolymer comprising monomers selected from Neu5Ac, Neu5Gc, and Kdn, or the polysialic acid can be a heteropolymer comprising 2 or 3 monomers selected from Neu5Ac, Neu5Gc, and Kdn. In certain specific embodiments, the homopolymer comprises Neu5Ac monomers. The homopolymer can be a poly(Neu5Ac)n, a poly(Neu5Gc)n, or a poly(Kdn)n polymer, wherein n is an integer greater than 10, greater than 15, or greater than 20; and optionally, wherein the monomers are 2→8 linked, 2→9 linked, or a combination thereof. In yet other specific embodiments, the heteropolymer comprising Neu5Ac and Neu5Gc monomers.

The polysialic acid can be a branched or unbranched polymer. An "unbranched" polymer is straight-chain polysialic acid polymer comprising a linear sequence of monomers. A "branched" polymer is a polysialic acid polymer that comprises a main chain with one more substituent side chains or branched. An example of a branched polymer is one that comprises a sialic acid unit bonded to three or more different sialic acid units, thereby creating a branch point within the polysialic acid.

The polysialic acid can, for example, have a molecular weight of at least 500 Da, at least 1 kDa, at least 3 kDa, at least 5 kDa, at least 10 kDa, at least 20 kDa, at least 25 kDa, at least 30 kDa, at least 40 kDa, at least 50 kDa, at least 60 kDa, at least 70 kDa, at least 75 kDa, at least 80 kDa, at least 90 kDa, at least 100 kDa, etc.

Preferably, said polysialic acid has a molecular weight of from 50 to 50,000,000, from 100 to 5,000,000, or from 500 to 500,000 Da.

In some embodiments, the polysialic acid is a polysialic acid comprising only sialic acid repeating units. This type of polymer is often referred as a "homopolymer." One example of such homopolymer of polysialic acid is colominic acid, commercially available from Carbosynth, Oakbrook Terrace, IL, USA. Colominic acid, also referred as polysialic acid, is a linear small polysaccharide containing α-2,8-linked sialic acid (neuraminic acid) with (n=8 to >100) residues.

In some embodiment, the polysialic acid is a "copolymer" comprising sialic acid repeating units and the repeating units of at least one different chemical entity. Non-limiting examples of such copolymers include PLGA-PSia, PEG- PSia, PLGA-PEG-PSia, etc. Here, PLGA is poly(lactide-co-glycolide), PEG is polyethylene glycol and PSia is polysialic acid.

In some embodiment, said polysialic acid is an oligomer of sialic acid, such as a dimer, a trimer, a tetramer, a pentamer and a hexamer available as N-acetylneuraminic acid oligomers or their sodium salts, available from Nacalai USA, Inc., San Diego, CA, United States.

In some embodiment, said polysialic acid is a pharmaceutically acceptable polymer having a sialic acid moiety at the terminal of its chemical structure. For example, PEG-Sia, or PLGA-PEG-Sia, where Sia represents the sialic acid moiety.

The sialic acid can also be a water-soluble salt and water-soluble derivative of sialic acid. For example, the sialic acid salt can be the sodium salt, the potassium salt, the magnesium salt, the calcium salt, or the zinc salt. As described above, the polysialic acid can comprising a combination of more than one type of sialic acid.

In one set of embodiments, one or more of sialic acid monomers within the polysialic acid is modified. For example, one or more sialic acid units can be modified by attachment to polyethylene glycol, or an alkyl group. In other embodiments, the polysialic acid is not modified.

The polysialic acid can also comprise other monomers or units in addition to sialic acid monomer. In certain examples, the polysialic acid is a conjugate of a polymer of sialic acid monomer units and another polymer, for example, a synthetic polymer, including for example, polyethylene glycol (PEG) (e.g., a polysialic acid-PEG copolymer). An example of such a conjugate has been described, for example, in Zhang et al. (2018), Drug Delivery and Translational Research 8, 602-616. The PEG can have the formula: $H—(O—CH_2—CH_2)n$-OH, where n is an integer representing the PEG polymerization degree. For example, n is at least 2, at least 4, at least 6, at least 8, at least 10, at least 15, at least 20, at least 25, at least 30, at least 40, at least 50, at least 75, at least 100, at least 200, at least 300, at least 400, or at least 500. In some cases, n is no more than 1000, no more than 500, no more than 200, no more than 100, no more than 50, no more than 30, or no more than 10.

The polysialic acids in a particle can be the same or can be different.

In addition, the polysialic acid can be substituted covalently or ionically along the length of the chain or at the termini of the chain. For example, one or more monomer units can be substituted by a targeting moiety, such as a cell ligand (or fragment), peptide, or carbohydrate. The substitution or conjugation step of the targeting moiety can occur before the nanoparticle is formed or after.

Cationic Lipid

Thus, a lipid may have a positive or partial positive charge at physiological pH. Such lipids may be referred to as cationic or ionizable (amino)lipids. Lipids may also be zwitterionic, i.e., neutral molecules having both a positive and a negative charge.

In some embodiments, the lipid can be selected from, for example, Dioleoyl-3-trimethylammonium propane (DOTAP), 1,2-di-O-octadecenyl-3-trimethylammonium propane (DOTMA), 3-(didodecylamino)-N1,N1,4-tridodecyl-1-piperazineethanamine (KL10), N1-[2-(didodecylamino)ethyl]-N1,N4,N4-tridodecyl-1,4-piperazinediethanami-ne (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)[1,3]-dioxolane (DLin-KC2-DMA), 1,2-dioleyloxy-N,N-dimethylaminopropane (DODMA), 2-({8-[(3.beta.)-cholest-5-en-3-yloxy]octyl}oxy)-N,N-dimethyl-3-[(9Z, 12Z)-octadeca-9,12-dien-1-yl oxy]propan-1-amine (Octyl-CLinDMA), (2R)-2-({8-[(3.beta.)-cholest-5-en-3-yloxy] octyl})oxy)-N,N-dimethyl-3-[(9-Z,12Z)-octadeca-9,12-dien-1-yloxy]propan-1-amine (Octyl-CLinDMA (2R)), and (2S)-2-({8-[(3.beta.)-cholest-5-en-3-yloxy]octyl}oxy)-N,N-dimethyl-3-[(9Z-,12Z)-octadeca-9,12-dien-1-yloxy]propan-1-amine (Octyl-CLinDMA (2S)).

Polyethylene Glycol (PEG) Lipids can also be used. The term "PEG lipid" refers to polyethylene glycol (PEG)-modified lipids. Non-limiting examples of PEG lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. In some embodiments, a PEG lipid can be PEG-c-DOMG, PEG-DMG, PEG-DLPE, PEG-DMPE, PEG-DPPC, or a PEG-DSPE lipid.

Lipids that can be used in the present invention as the complexing agent may be cationic lipids. Cationic lipids are amphiphilic molecules that have a cationic head group and a hydrophobic tail group connected by either stable or degradable linkages. Guanidine, imidazole, pyridinium, piperizine, and amino acid (e.g., lysine, arginine, ornithine, and tryptophan) are common head groups used in lipid modification. Lipids that can be used as complexing agent in the present invention include but not limit to monovalent aliphatic lipids with single amine functionality in their head group, e.g., N[1-(2,3-dioleyloxy)propyl]-N,N,N-trimethylammonium chloride (DOTMA),), N-(2-hydroxyethyl)-N,N-dimethyl-2,3-bis(tetradecyloxy-1-propanaminiumbromide) (DMRIE), Dimethyldioctadecylammonium (DDAB), ethyl PC's, pH sensitive lipids, multivalent aliphatic lipids with several amine functionalities in head group, e.g., spermine groups, e.g., dioctadecylamidoglycylspermine (DOGS), $N^4$—Cholesteryl-Spermine HCl Salt (GL67) or cationic cholesterol derivatives, e.g., 3b-[N—(N0, N0-dimethylaminoethane) carbamoyl] cholesterol (DC-Chol), bis-guanidium-tren-cholesterol (BGTC), and neutral helper lipids such as 1,2-dioleyl-sn-glycerol-3-phosphoethanolamine (DOPE) or cholesterol, which were added to complex of DNA and RNA and cationic lipids to improve transfection efficiency.

An ionizable lipid is a class of lipid molecules that are neutral and non-ionic at physiological pH, but will be protonated to become positively charged at lower pHs. Ionizable lipids can also form the complex with the SA-containing entity while promoting endosome escape and reducing toxicity. Examples of commercially available ionizable lipids include DLin-KC2-DMA, DLin-MC3-DMA, DLin-DMA, DODMA, and DODAP.

In order to increase the stability, functionality and other performance properties of the complex nanoparticles, other chemical entities commonly used in lipid nanoparticle (LNP) formulations such as structural lipids, PEGylated lipids, cholesterol, phospholipids, etc. may be added to the nanoparticle formulations of the present invention.

Cationic Polymer

Polymeric complexing agents can be cationic polymers comprising one or more cationic monomers and include polylysine, cell-penetrating peptides (such as polyarginine), polyethyleneimine, chitosan, and poly(amino ester).

Polylysine is a cationic homopolypeptide and can be an α-polylysine or ε-polylysine. Polylysine contains a positively charged amino group at neutral pH. α-Polylysine is a synthetic polymer and can be in the form of poly-L-lysine (PLL) and poly-D-lysine (PDL), respectively. ε-Polylysine (ε-poly-L-lysine, EPL) is typically produced as a homopolypeptide of approximately 25-30 L-lysine residues. Polylysine used in the present invention can be a copolymer of lysine and other chemical entity. Polylysine can also be modified to possess specific properties. For example, modified polylysine may be more hydrophobic by, for example, alkylating or acylating an amine group on one or more lysines.

Cell-penetrating peptides (CPPs) have the ability to translocate the plasma membrane and facilitate the delivery of various molecular cargoes to the cytoplasm or an organelle. Some cell-penetrating peptides such as polyarginine are cationic and are suitable as complexing agent for nucleic acids.

Polyethyleneimine (PEI) is a polymer with a repeating unit composed of an amine group and two carbon aliphatic ($CH_2CH_2$) spacer. There are linear and branched PEIs. The linear structure facilitates crystallization of the polymer and, as a result, linear PEIs can be crystalline and solid at room temperatures. Branched PEIs can be liquid at room temperatures. Linear PEIs contain primarily secondary amines, in contrast to branched PEIs which contain primary, secondary and tertiary amino groups.

Chitosan is a linear polysaccharide composed of randomly distributed β-(1→4)-linked D-glucosamine (deacetylated unit) and N-acetyl-D-glucosamine. The amino group in chitosan has a pKa value of ~6.5, which leads to significant protonation in neutral solution and a positive charge. Thus, chitosan can be used to form complexes with nucleic acid via ionic interaction.

Preferred poly(amino ester)s are biodegradable and biocompatible polymers. One example of poly(amino ester) is poly[α-(4-aminobutyl)-1-glycolic acid].

Poly(β-amino ester)s (PBAEs) are a class of polymers obtained from di-acrylates and functional amines including a primary and a secondary amine, preferably formed via Michael addition reaction. PBAEs are pH-sensitive, biodegradable and biocompatible. The pH buffering capability of PBAEs, which results from the presence of tertiary amines in the PBAE structure, facilitates endosomal escape and hence intracellular delivery of therapeutics.

Poly(amidoamine), or PAMAM, is a class of dendrimer which is made of repetitively branched subunits of amide and amine functionality.

The cationic complexing agents can also be modified to render other desired properties. For example, the cationic complexing agents, such as PBAE, can be PEGylated, thereby extending the in vivo circulation time. The cationic complexing agents, particularly polymers, can be optimized for molecule weight, degradation profile, in vivo half-life, pH responsiveness, and other properties that may be desired for specific applications.

Active Agent

The particles described can further comprise an active agent. The composition can comprise an API, and the API can be covalently or ionically attached to the surface of the nanoparticles via covalent bonds, such as a bond formed between an amide group of a protein and a carboxyl group on the surface of the nanoparticle. The API can also be encapsulated within the nanoparticles. The amount of the API can be about 0.01 to about 50% (w/w) of the nanoparticle, or about 0.05 to about 25%, about 0.1 to about 10%, about 0.2 to about 5%, about 0.5 to about 3%, about 1 to about 5%, or about 2 to about 5% (w/w) of the nanoparticle.

In certain aspects, the active agent is advantageously a drug (also referred to herein as an active pharmaceutical ingredient, or API). However, active agents that are non-therapeutic can also be included as part of the particles according to the methods. For example, agents useful in diagnostics, agriculture, cosmetics, personal products, home products, industrial chemicals, dyes, fluorescing agents or coloring agents and the like can be included. Preferred active ingredients include small molecules and macromolecules. For example, biomolecules, such as peptides, peptidomimetics, oligonucleotides, nucleic acid molecules and mimics thereof, such as DNA, RNA, PNA, siRNA, microRNA, antisense, proteins, antibodies and antigen binding fragments thereof, enzymes, hormones, growth factors, antigens, neoantigens, saccharides, oligosaccharides, polysaccharides, and a combination thereof. The composition can be free from other active pharmaceutical ingredients or API, such as attached peptide or antigenic moieties. It is understood that an API can be substituted with non-therapeutic compounds, such as diagnostic, agricultural, or chemical agents. Therefore, in each instance where the term API is used, it shall be understood that the term "active agent," including diagnostic, agricultural or chemical agents can be used in lieu thereof. The term "API" and "drug" are used interchangeably herein.

The API can be water-soluble or have relatively poor water-solubility. For example, a poorly water-soluble API may be dissolved in the same solvent used to dissolve the cationic lipid or polymer or the SA agent.

An API or active agent can include a wide variety of different compounds, including chemical compounds and mixtures of chemical compounds, e.g., small organic or inorganic molecules; saccharins; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof. Preferably, the therapeutic agent is a small molecule.

As used herein, the term "small molecule" can refer to compounds that are "natural product-like," however, the term "small molecule" is not limited to "natural product-like" compounds. Rather, a small molecule is typically characterized in that it contains several carbon-carbon bonds and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

As used herein a "peptide" is an oligopeptide, for example, a sequence of 2 to 25 amino acids. The term "peptide", unless otherwise specified, includes in its scope a peptide that contains an already known analog of a naturally-occurring amino acid having a function as well as the naturally-occurring amino acid. A "protein" comprises one or more peptide (polypeptide) chains and can comprise more amino acids than a peptide. The terms "peptide," "polypeptide," and "protein," may be used interchangeably herein.

Exemplary therapeutic agents include, but are not limited to, those approved by the FDA, subject to a new drug application with the FDA, in clinical trials or in preclinical research.

APIs include the herein disclosed categories and specific examples. It is not intended that the category be limited by the specific examples. Those of ordinary skill in the art will recognize also numerous other compounds that fall within the categories and that are useful according to the present disclosure. Examples include a radiosensitizer, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an anti-parkinsonian agent, an anti-angina/antihypertensive agent, an anticoagulant agent, an antiplatelet agent, a sedative, an anxiolytic agent, a peptidic agent, a biopolymeric agent, an antineoplastic agent, a laxative, an antidiarrheal agent, an antimicrobial agent, an antifungal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; anti-inflammatory agents, including anti-asthmatic anti-inflammatory agents, anti-arthritis anti-inflammatory agents, and non-steroidal anti-inflammatory agents, examples of which include but are not limited to sulfides, mesalamine, budesonide, salazopyrin, diclofenac, pharmaceutically acceptable diclofenac salts, nimesulide, naproxen, acetaminophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; anti-angina agents and antihypertensive agents such as isosorbide mononitrate, isosorbide dinitrate, propranolol, atenolol and verapamil; anticoagulant and antiplatelet agents such as Coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hydrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides.

Examples of suitable APIs include infliximab, etanercept, bevacizumab, ranibizumab, adalimumab, certolizumab pegol, golimumab, Interleukin 1 (IL-1) blockers such as anakinra, T cell costimulation blockers such as abatacept, Interleukin 6 (IL-6) blockers such as tocilizumab; Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/.beta.2 blockers such as Anti-lymphotoxin alpha (LTa) or anti-VEGF agents and the like.

Drugs or API include proteins or peptides, including but not limited, monoclonal antibodies (e.g., humanized, human, and/or mouse/human chimeric), polyclonal antibodies, and antibody-drug conjugates. Exemplary peptide/protein therapeutics include insulin, etanercept, pegfilgrastim, salmon calcitonin, cyclosporine, octreotide, liraglutide, bivalirudin, desmopressin, C1 esterase inhibitor (RUCONSET®), human glucocerebrosidase (ELELYSO®), humanized anti-CD20 monoclonal antibody (GAVYZA®), VEGFR Fc-fusion (EYLEA®), glucagon-like peptide-1 receptor agonist Fc-fusion (TRULICITY®), VEGFR Fc-fusion (ZALTRAP), Recombinant factor IX Fc fusion (ALPROLIX), Recombinant factor VIII Fc-fusion (ELOCTATE), GLP-1 receptor agonist-albumin fusion (TANZEUM®), Recombinant factor IX albumin fusion (IDELIVION®), PEGylated IFNb-1a (PLEGRIDY®), Recombinant factor VIII PEGylated (ADYNOVATE®), humanized anti-HER2/neu conjugated to emtansine (KADCYLA®), belimumab, ipilimumab, belatacept, brentuximab vedotin, aflibercept, asparaginase erwinia chrsanthemi, glucarpidase, taliglucerase alfa, pertuzumab, ziv-afilbercept, tbo-filgrastm, ocriplasmin, raxibacumab, ado-trastuzmab emtansine, golimumab, tocilizumab, Obinutuzumab, elosulfase alfa, metreleptin, albiglutide, ramucirumab, siltuxiumab, vedolizumab, peginterferon beta-1a, pembrolizumab, dulaglutide, bintumomab, nivolumab, secukinumab, parathyroid hormone, filgrastim-sndz, dinutuximab, alirocumab, evolocumab, idaracizumab, asfotase-alfa, mepolizumab, dratumumab, necitumumab, elotuzumab, sebelipase alfa, obiltoxaximab, ixekizumab, reslizumab, infliximab-dyyb, atezolizumab, daclizumab, etancerpt-szzs, coagulation factor IX recombinant human, antihemophilic factor (recombinant), coagulation factor XIII A-subunit (recombinant), coagulation factor IX (recombinant), Fc fusion protein, antihemophilic factor (recombinant), Fc fusion protein, C1 esterase inhibitor recombinant, antihemophilic factor porcine, B-domain truncated recombinant, coagulation factor IX (recombinant), antihemophilic factor (recombinant), antihemophilic factor (recombinant) PEGylated, von Willebrand factor (recombinant), coagulation factor IX recombinant human, and antihemophilic factor (recombinant).

The present invention is particularly applicable to the administration of anti-cancer agents. For example, the agent can be a DNA demethylating agents 5-azacytidine (azacitidine) or 5-aza-2'-deoxycytidine (decitabine), (Cytarabine or ara-C); pseudoiso-cytidine (psi ICR); 5-fluoro-2'-deoxycytidine (FCdR); 2'-deoxy-2',2'-difluorocytidine (Gemcitabine); 5-aza-2'-deoxy-2',2'-difluorocytidine; 5-aza-2'-deoxy-2'-fluorocytidine; Zebularine; 2',3'-dideoxy-5-fluoro-3'-thiacytidine (Emtriva); 2'-cyclocytidine (Ancitabine); Fazarabine or ara-AC; 6-azacytidine (6-aza-CR); 5,6-dihydro-5-azacytidine (dH-aza-CR); N.sup.4-pentyloxy-carbonyl-5'-deoxy-5-fluorocytidine (Capecitabine); $N^4$-octadecyl-cytarabine; or elaidic acid cytarabine. The cytidine analog can also be structurally related to cytidine or deoxycytidine and functionally mimics and/or antagonizes the action of cytidine or deoxycytidine. The agents can also include 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celecoxib, chlorambucil, cisplatinum, COX-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, DM1, DM3, DM4, doxorubicin, 2-pyrrolinodoxorubicine (2-PDox), a pro-drug form of 2-PDox (pro-2-PDox), cyano-morpholino doxorubicin, doxorubicin glucuronide, endostatin, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, monomethylauristatin F (MMAF), monomethylauristatin D (MMAD), monomethylauristatin E (MMAE), navelbine, neratinib, nilotinib, nitrosurea, olaparib, plicomycin, procarbazine, paclitaxel, PCI-32765, pentostatin, PSI-341, raloxifene, semustine, SN-38, sorafenib, streptozocin, SU11248, sunitinib, tamoxifen, temazolomide, transplatinum, thalidomide, thioguanine, thiotepa, teniposide, topotecan, uracil mustard, vatalanib, vinorelbine, vinblastine, vincristine, vinca alkaloids and ZD1839 or a pharmaceutically acceptable salt thereof.

The anticancer agents include, but are not limited to, an inhibitor, agonist, antagonist, ligand, modulator, stimulator, blocker, activator or suppressor of a gene, ligand, receptor, protein, factor such as an adenosine receptor (such as A2B, A2a, A3), Abelson murine leukemia viral oncogene homolog 1 gene (ABL, such as ABL1), Acetyl-CoA carboxylase (such as ACC1/2), adrenocorticotropic hormone receptor (ACTH), activated CDC kinase (ACK, such as ACK1), Adenosine deaminase, Adenylate cyclase, ADP ribosyl cyclase-1, Aerolysin, Angiotensinogen (AGT) gene, murine thymoma viral oncogene homolog 1 (AKT) protein kinase (such as AKT1, AKT2, AKT3), AKT1 gene, Alkaline phosphatase, Alpha 1 adrenoceptor, Alpha 2 adrenoceptor, Alpha-ketoglutarate dehydrogenase (KGDH), Aminopeptidase N, Arginine deiminase, Beta adrenoceptor, Anaplastic lymphoma kinase receptor, anaplastic lymphoma kinase (ALK, such as ALK1), Alk-5 protein kinase, AMP activated protein kinase, Androgen receptor, Angiopoietin (such as ligand-1, ligand-2), apolipoprotein A-I (APOA1) gene, apoptosis signal-regulating kinase (ASK, such as ASK1), Apoptosis inducing factor, apoptosis protein (such as 1, 2), Arginase (I), asparaginase, Asteroid homolog 1 (ASTE1) gene, ataxia telangiectasia and Rad 3 related (ATR) serine/threonine protein kinase, Axl tyrosine kinase receptor, Aromatase, Aurora protein kinase (such as 1, 2), Basigin, BCR (breakpoint cluster region) protein and gene, B-cell lymphoma 2 (BCL2) gene, Bc12 protein, Bc12 binding component 3, BCL2L11 gene, Baculoviral IAP repeat containing 5 (BIRCS) gene, B-Raf proto-oncogene (BRAF), Brc-Abl tyrosine kinase, Beta-catenin, B-lymphocyte antigen CD19, B-lymphocyte antigen CD20, B-lymphocyte stimulator ligand, B-lymphocyte cell adhesion molecule, Bone morphogenetic protein-10 ligand, Bone morphogenetic protein-9 ligand modulator, Brachyury protein, Bradykinin receptor, Bruton's tyrosine kinase (BTK), Bromodomain and external domain (BET) bromodomain containing protein (such as BRD2, BRD3, BRD4), Calmodulin, calmodulin-dependent protein kinase (CaMK, such as CAMKII), Cancer testis antigen 2, Cancer testis antigen NY-ESO-1, Cannabinoid receptor (such as CB1, CB2), Carbonic anhydrase, caspase 8 apoptosis-related cysteine peptidase CASP8-FADD-like regulator, Caspase (such as caspase-3, caspase-7, Caspase-9), Caspase recruitment domain protein-15, Cathepsin G, chemokine (C—C motif) receptor (such as CCR2, CCR4, CCR5), CCR5 gene, Chemokine CC21 ligand, cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e, CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; Chorionic gonadotropin, Cyclin G1, Cyclin D1, cyclin-dependent kinases (CDK, such as CDK1, CDK1B, CDK2-9), casein kinase (CK, such as CM, CMI), c-Kit (tyrosine-protein kinase Kit or CD117), c-Met (hepatocyte growth factor receptor (HGFR)), CDK-activating kinase (CAK), Checkpoint kinase (such as CHK1, CHK2), Cholecystokinin CCK2 receptor, Claudin (such as 6, 18), Clusterin, Complement C3, COP9 signalosome subunit 5, CSF-1 (colony-stimulating factor 1 receptor), CSF2 gene, clusterin (CLU) gene, Connective tissue growth factor, cyclooxygenase (such as 1, 2), cancer/testis antigen 1B (CTAG1) gene, CTLA-4 (cytotoxic T-lymphocyte protein 4) receptor, CYP2B1 gene, Cysteine palmitoyltransferase porcupine, cytokine signalling-1, cytokine signalling-3, Cytochrome P450 11B2, Cytochrome P450 reductase, cytochrome P450 3A4, cytochrome P450 17A1, Cytochrome P450 17, Cytochrome P450 2D6, (provided the anticancer or cytrochrome modifying agents are something other than cobicistat), Cytoplasmic isocitrate dehydrogenase, Cytosine deaminase, cytosine DNA methyltransferase, cytotoxic T-lymphocyte protein-4, chemokine (C—X—C motif) receptor (such as CXCR4, CXCR1 and CXCR2), Delta-like protein ligand (such as 3, 4), Deoxyribonuclease, Dickkopf-1 ligand, Dihydropyrimidine dehydrogenase, DNA binding protein (such as HU-beta), DNA dependent protein kinase, DNA gyrase, DNA methyltransferase, DNA polymerase (such as alpha), DNA primase, discoidin domain receptor (DDR, such as DDR1), DDR2 gene, dihydrofolate reductase (DHFR), Dipeptidyl peptidase IV, L-dopachrome tautomerase, dUTP pyrophosphatase, echinoderm microtubule like protein 4, epidermal growth factor receptor (EGFR) gene, EGFR tyrosine kinase receptor, Eukaryotic translation initiation factor 5A (EIFSA) gene, Elastase, Elongation factor 1 alpha 2, Elongation factor 2, Endoglin, Endonuclease, Endoplasmin, Endosialin, Endostatin, endothelin (such as ET-A, ET-B), Enhancer of zeste homolog 2 (EZH2), epidermal growth factor, epidermal growth factor receptors (EGFR), Epithelial cell adhesion molecule (EpCAM), Ephrin (EPH) tyrosine kinase (such as Epha3, Ephb4), Ephrin B2 ligand, Epigen, Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, Extracellular signal-regulated kinases (ERK), E-selectin, Estradiol 17 beta dehydrogenase, Estrogen receptor (such as alpha, beta), Estrogen related receptor, Exportin 1, Extracellular signal related kinase (such as 1, 2), Factor (such as Xa, VIIa), Fas ligand, Fatty acid synthase, Ferritin, focal adhesion kinase (FAK, such as FAK2), fibroblast growth factor (FGF, such as FGF1, FGF2, FGF4), FGF-2 ligand, FGF-5 ligand, Fibronectin, Fms-related tyrosine kinase 3 (Flt3), farnesoid x receptor (FXR), Folate, Folate transporter 1, Folate receptor (such as alpha), folate hydrolase prostate-specific membrane antigen 1 (FOLH1), paired basic amino acid cleaving enzyme (FURIN), FYN tyrosine kinase, Galactosyltransferase, Galectin-3, glucocorticoid-induced TNFR-related protein GITR receptor, Glucocorticoid, Beta-glucuronidase, Glutamate carboxypeptidase II, glutaminase, Glutathione S-transferase P, Glypican 3 (GPC3), glycogen synthase kinase (GSK, such as 3-beta), Granulocyte-colony stimulating factor (GCSF) ligand, Granulocyte macrophage colony stimulating factor (GM-CSF) receptor, gonadotropin-releasing hormone (GNRH), growth factor receptor-bound protein 2 (GRB2), molecular chaperone groEL2 gene, Grp78 (78 kDa glucose-regulated protein) calcium binding protein, Imprinted Maternally Expressed Transcript (H19) gene, Heat stable enterotoxin receptor, Heparanase, Hepatocyte growth factor, Heat shock protein gene, Heat shock protein (such as 27, 70, 90 alpha, beta), Hedgehog protein, HERV-H LTR associating protein 2, Hexose kinase, tyrosine-protein kinase HCK, Histamine H2 receptor, histone deacetylase (HDAC, such as 1, 2, 3, 6, 10, 11), Histone H1, Histone H3, Histone methyltransferase (DOT1L), Human leukocyte antigen (HLA), HLA class I antigen (A-2 alpha), HLA class II antigen, Homeobox protein NANOG, mitogen-activated protein kinase kinase 1 (MAP4K1, HPK1), HSPB1 gene, Human papillomavirus (such as E6, E7) protein, Hyaluronidase, Hyaluronic acid, Hypoxia inducible factor-1 alpha, Intercellular adhesion molecule 1 (ICAM-1), immunoglobulin (such as G, G1, G2, K, M), indoleamine 2,3-dioxygenase (IDO, such as IDO1), indoleamine pyrrole 2,3-dioxygenase 1 inhibitor, I-Kappa-B kinase (IKK, such as IKK.beta.epsilon.), Immunoglobulin Fc receptor, Immunoglobulin gamma Fc receptor (such as I, III, IIIA), Interleukin 1 ligand, interleukin 2 ligand, Interleukin-2, IL-2 gene, IL-1 alpha, IL-1 beta, IL-2, IL-2 receptor alpha subunit, IL-3 receptor, IL-4, IL-6, IL-7, IL-8, IL-12, IL-15, IL-12 gene, IL-17, Interleukin 13 receptor alpha 2, Interleukin-29 ligand, interleukin-1 receptor-associated kinase 4 (IRAK4), Insulin-like growth factor (such as 1, 2), insulin receptor, Integrin alpha-V/beta-3, Integrin alpha-V/beta-5, Integrin alpha-V/beta-6, Integrin alpha-5/beta-1, Integrin alpha-4/beta-1, integrin alpha-4/beta-7, Interferon inducible protein absent in melanoma 2 (AIM2), interferon (such as alpha, alpha 2, beta, gamma), interferon type I receptor, isocitrate dehydrogenase (such as IDH1, IDH2), Janus kinase (JAK, such as JAK1, JAK2), Jun N terminal kinase, Kinase insert domain receptor (KDR), Killer cell Ig like receptor, Kisspeptin (KISS-1) receptor, v-kit Hardy-Zuckerman 4 feline sarcoma viral oncogene homolog (KIT) tyrosine kinase, KIT gene, Kinesin-like protein KIF11, kallikrein-related peptidase 3 (KLK3) gene, Kirsten rat sarcoma viral oncogene homolog (KRAS) gene, lactoferrin, lymphocyte activation gene 3 protein (LAG-3), lysosomal-associated membrane protein family (LAMP) gene, Lanosterol-14 demethylase, LDL receptor related protein-1, Leukotriene A4 hydrolase, Listeriolysin, L-Selectin, Luteinizing hormone receptor, Lyase, Lymphocyte antigen 75, lysine demethylases (such as KDM1, KDM2, KDM4, KDM5, KDM6, A/B/C/D), Lymphocyte function antigen-3 receptor, lymphocyte-specific protein tyrosine kinase (LCK), Lymphotactin, Lyn (Lck/Yes novel) tyrosine kinase, Lysophosphatidate-1 receptor, lysyl oxidase protein (LOX), lysyl oxidase-like protein (LOXL, such as LOXL2), Lysyl oxidase homolog 2, Macrophage migration inhibitory fact, melanoma antigen family A3 (MAGEA3) gene, MAGEC1 gene, MAGEC2 gene, Major vault protein, myristoylated alanine-rich protein kinase C substrate (MARCKS) protein, Melan-A (MART-1) melanoma antigen, Mas-related G-protein coupled receptor, matrix metalloprotease (MMP, such as MMP2, MMP9), myeloid cell leukemia 1 (MCL1) gene, Mcl-1 differentiation protein, macrophage colony-stimulating factor (MCSF) ligand, Melanoma associated antigen (such as 1, 2, 3, 6), melanocyte stimulating hormone ligand, Melanocyte protein Pmel 17, Membrane copper amine oxidase, Mesothelin, Metabotropic glutamate receptor 1, mitogen-activated protein kinase (MEK, such as MEK1, MEK2), Hepatocyte growth factor receptor (MET) gene, MET tyrosine kinase, methionine aminopeptidase-2, mitogen-activate protein kinase (MAPK), Mdm2 p53-binding protein, Mdm4 protein, Metalloreductase STEAP1 (six transmembrane epithelial antigen of the prostate 1), Metastin, Methyltransferase, Mitochondrial 3 ketoacyl CoA thiolase, MAPK-activated protein kinase (such as MK2), mTOR (mechanistic target of rapamycin (serine/threonine kinase), mTOR complex (such as 1, 2), mucin (such as 1, 5A, 16), mut T homolog (MTH, such as MTH1), Myc proto-oncogene protein, NAD ADP ribosyltransferase, natriuretic peptide receptor C, Neural cell adhesion molecule 1, Neurokinin receptor, Neuropilin 2, Nitric oxide synthase, Nuclear Factor (NF) kappa B, NF kappa B activating protein, Neurokinin 1 (NK1) receptor, NK cell receptor, NK3 receptor, NKG2 A B activating NK receptor, NIMA-related kinase 9 (NEK9), Noradrenaline transporter, Notch (such as Notch-2 receptor, Notch-3 receptor), nucleophosmin-anaplastic lymphoma kinase (NPM-ALK), 2,5-oligoadenylate synthetase, Nuclear erythroid 2-related factor 2, Nucleolin, Nucleophosmin, O-methylguanine DNA methyltransferase, Ornithine decarboxylase, Orotate phosphoribosyltransferase, orphan nuclear hormone receptor NR4A1, Opioid receptor (such as delta), Osteocalcin, Osteoclast differentiation factor, Osteopontin, OX-40 (tumor necrosis factor receptor superfamily member 4 TNFRSF4, or CD134) receptor, 2 oxoglutarate dehydrogenase, purinergic receptor P2X ligand gated ion channel 7 (P2X7), Parathyroid hormone ligand, p53 tumor suppressor protein, P3 protein, Programmed cell death 1 (PD-1), Proto-oncogene serine/threonine-protein kinase (PIM, such as PIM-1, PIM-2, PIM-3), Poly ADP ribose polymerase (PARP, such as PARP1, 2 and 3), p38 kinase, p38 MAP kinase, platelet-derived growth factor (PDGF, such as alpha, beta), P-Glycoprotein (such as 1), Platelet-derived growth factor (PDGF, such as alpha, beta), PKN3 gene, P-Selectin, phosphatidylinositol 3-kinase (PI3K), phosphoinositide-3 kinase (PI3K such as alpha, delta, gamma), phosphorylase kinase (PK), placenta growth factor, Pleiotropic drug resistance transporter, Plexin B1, Polo-like kinase 1, peroxisome proliferator-activated receptors (PPAR, such as alpha, delta, gamma), Preferentially expressed antigen in melanoma (PRAME) gene, Probable transcription factor PML, Programmed cell death ligand 1 inhibitor (PD-L1), Progesterone receptor, prostate specific antigen, Prostatic acid phosphatase, Prostanoid receptor (EP4), proteasome, Protein farnesyltransferase, protein kinase (PK, such as A, B, C), Protein E7, protein tyrosine kinase, Protein tyrosine phosphatase beta, polo-like kinase (PLK), PLK1 gene, Prenyl-binding protein (PrPB), protoporphyrinogen oxidase, Prosaposin (PSAP) gene, phosphatase and tensin homolog (PTEN), Purine nucleoside phosphorylase, Pyruvate kinase (PYK), Pyruvate dehydrogenase (PDH), Pyruvate dehydrogenase kinase, Raf protein kinase (such as 1, B), RAF1 gene, Ras GTPase, Ras gene, 5-Alpha-reductase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS proto-oncogene 1, receptor tyrosine kinase) gene, Ros1 tyrosine kinase, Runt-related transcription factor 3, 5100 calcium binding protein A9, Sarco endoplasmic calcium ATPase, Gamma-secretase, Secreted frizzled related protein-2, Semaphorin-4D, SL cytokine ligand, Serine protease, Signaling lymphocytic activation molecule (SLAM) family member 7, spleen tyrosine kinase (SYK), Src tyrosine kinase, tumor progression locus 2 (TPL2), serine/threonine kinase (STK), signal transduction and transcription (STAT, such as STAT-1, STAT-3, STAT-5), Second mitochondria-derived activator of caspases (SMAC) protein, smoothened (SMO) receptor, Sodium phosphate cotransporter 2B, Sodium iodide cotransporter, Somatostatin receptor (such as 1, 2, 3, 4, 5), Sonic hedgehog protein, Specific protein 1 (Sp1) transcription factor, Sphingomyelin synthase, Sphingosine-1-phosphate receptor-1, Sphingosine kinase (such as 1, 2), SRC gene, STAT3 gene, six-transmembrane epithelial antigen of the prostate (STEAP) gene, Steroid sulfatase, stimulator of interferon genes protein, Stimulator of interferon genes (STING) receptor, Stromal cell-derived factor 1 ligand, SUMO (small ubiquitin-like modifier), Superoxide dismutase, Survivin protein, Synapsin 3, Syndecan-1, Synuclein alpha, serine/threonine-protein kinase (TBK, such as TBK1), TATA box-binding protein-associated factor RNA polymerase I subunit B (TAF1B) gene, T-cell surface glycoprotein CD8, T-cell CD3 glycoprotein zeta chain, T-cell differentiation antigen CD6, T cell surface glycoprotein CD28, Tec protein tyrosine kinase, Tek tyrosine kinase receptor, telomerase, Tenascin, Telomerase reverse transcriptase (TERT) gene, Transforming growth factor (TGF, such as beta) kinase, TGF beta 2 ligand, T-cell immunoglobulin and mucin-domain containing-3 (TIM-3), Tissue factor, Tumor necrosis factor (TNF, such as alpha, beta), TNF related apoptosis inducing ligand, TNFR1 associated death domain protein, TNFSF9 gene, TNFSF11 gene, trophoblast glycoprotein (TPBG) gene, Transferrin, Tropomyosin receptor kinase (Trk) receptor (such as TrkA, TrkB, TrkC), Trophoblast glycoprotein, Thymidylate synthase, Tyrosine kinase with immunoglobulin-like and EGF-like domains (TIE) receptor, Toll-like receptor (TLR such as 1-13), topoisomerase (such as I, II, III), Tumor protein 53 (TP53) gene, Transcription factor, Transferase, Transforming growth factor TGF-.beta. receptor kinase, Transglutaminase, Translocation associated protein, Transmembrane glycoprotein NMB, Tumor necrosis factor 13C receptor, Thymidine kinase, Thymidine phosphorylase, Thymidylate synthase, Thymosin (such as alpha 1), Thyroid hormone receptor, Trop-2 calcium signal transducer, Thyroid stimulating hormone receptor, Tryptophan 5-hydroxylase, Tyrosinase, tyrosine kinase (TK), Tyrosine kinase receptor, Tyrosine protein kinase ABL1 inhibitor, tank-binding kinase (TBK), Thrombopoietin receptor, TNF-related apoptosis-inducing ligand (TRAIL) receptor, Tubulin, Tumor suppressor candidate 2 (TUSC2) gene, Tyrosine hydroxylase, Ubiquitin-conjugating enzyme E2I (UBE2I, UBC9), Ubiquitin, Ubiquitin carboxyl hydrolase isozyme L5, Ubiquitin thioesterase-14, Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Proto-oncogene tyrosine-protein kinase Yes, Wee-1 protein kinase, Wilms' tumor protein, Wilms' tumor antigen 1, X-linked inhibitor of apoptosis protein, Zinc finger protein transcription factor or any combination thereof.

The anticancer agent includes agents defined by their mechanism of action or class, including: anti-metabolites/anti-cancer agents such as pyrimidine analogs floxuridine, capecitabine, cytarabine, CPX-351 (liposomal cytarabine, daunorubicin), TAS-118; purine analogs, folate antagonists (such as pralatrexate), and related inhibitors; antiproliferative/antimitotic agents including natural products such as vinca alkaloid (vinblastine, vincristine) and microtubule such as taxane (paclitaxel, docetaxel), vinblastin, nocodazole, epothilones, vinorelbine) (NAVELBINE), and epipodophyllotoxins (etoposide, teniposide); DNA damaging agents such as actinomycin, amsacrine, busulfan, carboplatin, chlorambucil, cisplatin, cyclophosphamide) (CYTOXAN), dactinomycin, daunorubicin, doxorubicin, epirubicin, iphosphamide, melphalan, merchlorethamine, mitomycin C, mitoxantrone, nitrosourea, procarbazine, taxol, Taxotere, teniposide, etoposide, and triethylenethiophosphoramide; DNA-hypomethylating agent such as guadecitabine (SGI-110) antibiotics such as dactinomycin, daunorubicin, doxorubicin, idarubicin, anthracyclines, mitoxantrone, bleomycins, plicamycin (mithramycin), and; enzymes such as L-asparaginase which systemically metabolizes L-asparagine and deprives cells which do not have the capacity to synthesize their own asparagine; anti-platelet agents; a DNAi oligonucleotide targeting Bcl-2 such as PNT2258; agents that activate or reactivate latent human immunodeficiency virus (HIV) such as panobinostat or romidepsin asparaginase stimulators, such as crisantaspase (Erwinase®) and GRASPA (ERY-001, ERY-ASP); pan-Trk, ROS1 and ALK inhibitors such as entrectinib anaplastic lymphoma kinase (ALK) inhibitors such as alectinib antiproliferative/antimitotic alkylating agents such as nitrogen mustards cyclophosphamide and analogs (melphalan, chlorambucil, hexamethylmelamine, and thiotepa), alkyl nitrosoureas (carmustine) and analogs, streptozocin, and triazenes (dacarbazine); antiproliferative/antimitotic antimetabolites such as folic acid analogs (methotrexate); platinum coordination complexes (cisplatin, oxiloplatinim, and carboplatin), procarbazine, hydroxyurea, mitotane, and aminoglutethimide; hormones, hormone analogs (estrogen, tamoxifen, goserelin, bicalutamide, and nilutamide), and aromatase inhibitors (letrozole and anastrozole); anticoagulants such as heparin, synthetic heparin salts, and other inhibitors of thrombin; fibrinolytic agents such as tissue plasminogen activator, streptokinase, urokinase, aspirin, dipyridamole, ticlopidine, and clopidogrel; antimigratory agents; antisecretory agents (breveldin); immunosuppressives tacrolimus, sirolimus, azathioprine, and mycophenolate; compounds (TNP-470, genistein) and growth factor inhibitors (vascular endothelial growth factor inhibitors, and fibroblast growth factor inhibitors such as FPA14; angiotensin receptor blockers, nitric oxide donors; antisense oligonucleotides, such as AEG35156; DNA interference oligonucleotides, such as PNT2258, AZD-9150 antibodies such as trastuzumab and rituximab; anti-HER3 antibodies, such as LJM716 anti-HER2 antibodies such as margetuximab; anti-HLA-DR antibodies such as IMMU-114; anti-IL-3 antibodies, such as JNJ-56022473; anti-OX40 antibodies such as MEDI6469 anti-EphA3 antibodies, such as KB-004; an anti-CD20 antibody such as obinutuzumab; an anti-programmed cell death protein 1 (anti-PD-1) antibody such as nivolumab (OPDIVO, BMS-936558, MDX-1106), pembrolizumab (KEYTRUDA, MK-3477, SCH-900475, lambrolizumab, CAS Reg. No. 1374853-91-4), pidilizumab, and anti-programmed death-ligand 1 (anti-PD-L1) antibodies such as BMS-936559, atezolizumab (MPDL3280A), durvalumab (MEDI4736), avelumab (MSB0010718C), and MDX1105-01, CXCR4 antagonists such as BL-8040; CXCR2 antagonist such as AZD-5069; GM-CSF antibodies such as lenzilumab. Selective estrogen receptor downregulator (SERD) such as fulvestrant (Faslodex); a transforming growth factor-beta (TGF-beta) kinase antagonist such as galunisertib; a bispecific antibody such as MM-141 (IGF-1/ErbB3), MM-111 (Erb2/Erb3), JNJ-64052781 (CD19/CD3). Mutant selective EGFR inhibitors, such as PF-06747775, EGF816, ASP8273, ACEA-0010, BI-1482694. Alpha-ketoglutarate dehydrogenase (KGDH) inhibitors such as CPI-613, XPO1 inhibitors such as selinexor (KPT-330). Isocitrate dehydrogenase 2 (IDH2) inhibitors such as enasidenib (AG-221), and IDH1 inhibitors such as AG-120, and AG-881 (IDH1 and IDH2). Agents that target the interleukin-3 receptor (IL-3R) such as SL-401. Arginine deiminase stimulators, such as pegargiminase (ADI-PEG-20) antibody-drug conjugates, such as MLN0264 (anti-GCC, guanylyl cyclase C), T-DM1 (trastuzumab emtansine, Kadcycla), milatuzumab-doxorubicin (hCD74-DOX), brentuximab vedotin, DCDT2980S, polatuzumab vedotin, SGN-CD70A, SGN-CD19A, inotuzumab ozogamicin, lorvotuzumab mertansine, SAR3419, isactuzumab govitecan, anti-claudin-18.2 antibodies such as IMAB362.beta.-catenin inhibitors, such as CWP-291 a CD73 antagonist such as MEDI-9447; c-PIM inhibitors, such as PIM447, a BRAF inhibitor such as dabrafenib, vemurafenib, a sphingosine kinase-2 (SK2) inhibitor such as Yeliva. (ABC294640) cell cycle inhibitors such as selumetinib (MEK1/2), sapacitabine, AKT inhibitors such as MK-2206, ipatasertib, afuresertib, anti-CTLA-4 (cytotoxic T-lymphocyte protein-4) inhibitor such as tremelimumab, c-MET inhibitors, such as AMG-337, savolitinib, tivantinib (ARQ-197), capmatinib, tepotinib inhibitors of CSF1R/KIT and FLT3 such as PLX3397, a kinase inhibitor such as vandetanib; E selectin antagonists such as GMI-1271, differentiation inducers such as tretinoin; epidermal growth factor receptor (EGFR) inhibitors such as osimertinib (AZD-9291) topoisomerase inhibitors (doxorubicin, daunorubicin, dactinomycin, eniposide, epirubicin, etoposide, idarubicin, irinotecan, mitoxantrone, pixantrone, sobuzoxane, topotecan, and irinotecan, MM-398 (liposomal irinotecan), vosaroxin and corticosteroids (cortisone, dexamethasone, hydrocortisone, methylprednisolone, prednisone, and prednisolone); growth factor signal transduction kinase inhibitors; dysfunction inducers; nucleoside analogs such as DFP-10917 Axl inhibitors such as BGB-324; BET inhibitors such as INCB-054329, PARP inhibitors such as olaparib, rucaparib, veliparib, Proteasome inhibitors such as ixazomib, carfilzomib (Kyprolis); Glutaminase inhibitors such as CB-839; vaccines such as peptide vaccine TG-01 (RAS), bacterial vector vaccines such as CRS-207/GVAX, autologous Gp96 vaccine, dendritic cells vaccines, Oncoquest-L vaccine, DPX-Survivac, ProstAtak, DCVAC, ADXS31-142, demcizumab (anti-DLL4, Delta-like ligand 4, Notch pathway), napabucasin (BBI-608) smoothened (SMO) receptor inhibitors, such as Odomzo®. (sonidegib, formerly LDE-225), LEQ506, vismodegib (GDC-0449), BMS-833923, glasdegib (PF-04449913), LY2940680, and itraconazole; interferon alpha ligand modulators, such as interferon alfa-2b, interferon alpha-2a biosimilar (Biogenomics), ropeginterferon alfa-2b (AOP-2014, P-1101, PEG IFN alpha-2b), Multiferon (Alfanative, Viragen), interferon alpha 1b, Roferon-A (Canferon, Ro-25-3036), interferon alfa-2a follow-on biologic (Biosidus) (Inmutag, Inter 2A), interferon alfa-2b follow-on biologic (Biosidus-Bioferon, Citopheron, Ganapar) (Beijing Kawin Technology-Kaferon) (AXXO-interferon alfa-2b), Alfaferone, pegylated interferon alpha-1, peginterferon alfa-2b follow-on biologic (Amega), recombinant human interferon alpha-1, recombinant human interferon alpha-2a, recombinant human interferon alpha-2b, veltuzumab-IFN alpha 2b conjugate, Dynavax (SD-101), and interferon alfa-n1 (Humoferon, SM-10500, Sumiferon); interferon gamma ligand modulators, such as interferon gamma (OH-6000, Ogamma 100); IL-6 receptor modulators, such as tocilizumab, siltuximab, AS-101 (CB-06-02, IVX-Q-101); Telomerase modulators, such as tertomotide (GV-1001, HR-2802, Riavax) and imetelstat (GRN-163, JNJ-63935937) DNA methyltransferases inhibitors, such as temozolomide (CCRG-81045), decitabine, guadecitabine (S-110, SGI-110), KRX-0402, and azacitidine; DNA gyrase inhibitors, such as pixantrone and sobuzoxane; Bcl-2 family protein inhibitor ABT-263, venetoclax (ABT-199), ABT-737, and AT-101; Notch inhibitors such as LY3039478, tarextumab (anti-Notch2/3), BMS-906024 anti-myostatin inhibitors such as landogrozumab, hyaluronidase stimulators such as PEGPH-20, Wnt pathway inhibitors such as SM-04755, PRI-724, gamma-secretase inhibitors such as PF-03084014, IDO inhibitors such as indoximod, Grb-2 (growth factor receptor bound protein-2) inhibitor BP1001 (liposomal Grb-2), TRAIL pathway-inducing compounds, such as ONC201, Focal adhesion kinase inhibitors such as VS-4718, defactinib, hedgehog inhibitors such as saridegib, sonidegib (LDE225), glasdegib and vismodegib, Aurora kinase inhibitors such as alisertib (MLN-8237), modulators of HSPB1 activity (heat shock protein 27, HSP27), such as brivudine, apatorsen, ATR inhibitor such as AZD6738, and VX-970, mTOR inhibitors, such as sapanisertib, Hsp90 inhibitors such as AUY922. Murine double minute (mdm2) oncogene inhibitors such as DS-3032b CD137 agonist such as urelumab, Anti-KIR monoclonal antibodies such as lirilumab (IPH-2102). Antigen CD19 inhibitors such as MOR208, MEDI-551, AFM-11, CD44 binders such as A6, CYP17 inhibitors, such as VT-464, ASN-001, ODM-204. RXR agonists such as IRX4204, TLRs (Toll-like receptors) agonists such as IMO-8400 A hedgehog/smoothened (hh/Smo) antagonist such as taladegib. Immunomodulators such as complement C3 modulators, such as Imprime PGG. Intratumural immune-oncology agents such as G100 (TLR4 agonist) IL-15 agonists such as ALT-803 EZH2 (enhancer of zeste homolog 2) inhibitors such as tazemetostat. Oncolytic viruses, such as pelareorep, and talimogene laherparepvec). DOT1L (histone methyltransferase) inhibitors such as pinometostat (EPZ-5676), toxins such as Cholera toxin, ricin, *Pseudomonas* exotoxin, *Bordetella pertussis* adenylate cyclase toxin, diphtheria toxin, and caspase activators; and chromatin. DNA plasmid such as BC-819. PLK inhibitors of PLK 1, 2, and 3, such as volasertib (PLK1). Apoptosis Signal-Regulating Kinase (ASK) Inhibitors: ASK inhibitors include ASK1 inhibitors. Examples of ASK1 inhibitors include, but are not limited to, those described in WO 2011/008709 (Gilead Sciences) and WO 2013/112741 (Gilead Sciences). Bruton's Tyrosine Kinase (BTK) Inhibitors: Examples of BTK inhibitors include, but are not limited to, (S)-6-amino-9-(1-(but-2-ynoyl)pyrrolidin-3-yl)-7-(4-phenoxyphenyl)-7H-pur-in-8 (9H)-one, acalabrutinib (ACP-196), BGB-3111, HM71224, ibrutinib, M-2951, ONO-4059, PRN-1008, spebrutinib (CC-292), TAK-020. Cyclin-dependent Kinase (CDK) Inhibitors: CDK inhibitors include inhibitors of CDK 1, 2, 3, 4, 6 and 9, such as abemaciclib, alvocidib (HMR-1275, flavopiridol), AT-7519, FLX-925, LEE001, palbociclib, ribociclib, rigosertib, selinexor, UCN-01, and TG-02. Discoidin Domain Receptor (DDR) Inhibitors: DDR inhibitors include inhibitors of DDR1 and/or DDR2. Examples of DDR inhibitors include, but are not limited to, those disclosed in WO 2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO 2013/034933 (Imperial Innovations). Histone Deacetylase (HDAC) Inhibitors: Examples of HDAC inhibitors include, but are not limited to, abexinostat, ACY-241, AR-42, BEBT-908, belinostat, CKD-581, CS-055 (HBI-8000), CUDC-907, entinostat, givinostat, mocetinostat, panobinostat, pracinostat, quisinostat (JNJ-26481585), resminostat, ricolinostat, SHP-141, valproic acid (VAL-001), vorinostat. Janus Kinase (JAK) Inhibitors: JAK inhibitors inhibit JAK1, JAK2, and/or JAK3. Examples of JAK inhibitors include, but are not limited to, AT9283, AZD1480, baricitinib, BMS-911543, fedratinib, filgotinib (GLPG0634), gandotinib (LY2784544), INCB039110, lestaurtinib, momelotinib (CYT0387), NS-018, pacritinib (SB1518), peficitinib (ASP015K), ruxolitinib, tofacitinib (formerly tasocitinib), and XL019. Lysyl Oxidase-Like Protein (LOXL) Inhibitors: LOXL inhibitors include inhibitors of LOXL1, LOXL2, LOXL3, LOXL4, and/or LOXL5. Examples of LOXL inhibitors include, but are not limited to, the antibodies described in WO 2009/017833 (Arresto Biosciences). Examples of LOXL2 inhibitors include, but are not limited to, the antibodies described in WO 2009/017833 (Arresto Biosciences), WO 2009/035791 (Arresto Biosciences), and WO 2011/097513 (Gilead Biologics). Matrix Metalloprotease (MMP) Inhibitors: MMP inhibitors include inhibitors of MMP1 through 10. Examples of MMP9 inhibitors include, but are not limited to, marimastat (BB-2516), cipemastat (Ro 32-3555) and those described in WO 2012/027721 (Gilead Biologics). Mitogen-activated Protein Kinase (MEK) Inhibitors: MEK inhibitors include antroquinonol, binimetinib, cobimetinib (GDC-0973, XL-518), MT-144, selumetinib (AZD6244), sorafenib, trametinib (GSK1120212), uprosertib+trametinib. Phosphatidylinositol 3-kinase (PI3K) Inhibitors: PI3K inhibitors include inhibitors of PI3K.gamma., PI3K. delta., PI3.beta., PI3K.alpha., and/or pan-PI3K. Examples of PI3K inhibitors include, but are not limited to, ACP-319, AEZA-129, AMG-319, AS252424, BAY 10824391, BEZ235, buparlisib (BKM120), BYL719 (alpelisib), CH5132799, copanlisib (BAY 80-6946), duvelisib, GDC-0941, GDC-0980, GSK2636771, GSK2269557, idelalisib (Zydelig®), IPI-145, IPI-443, KAR4141, LY294002, Ly-3023414, MLN1117, OXY111A, PA799, PX-866, RG7604, rigosertib, RP5090, taselisib, TG100115, TGR-1202, TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences). Spleen Tyrosine Kinase (SYK) Inhibitors: Examples of SYK inhibitors include, but are not limited to, 6-(1H-indazol-6-yl)-N-(4-morpholinophenyl)imidazo[1,2-alpyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Conn.). and those described in U.S. 2015/0175616. Tyrosine-kinase Inhibitors (TKIs): TKIs may target epidermal growth factor receptors (EGFRs) and receptors for fibroblast growth factor (FGF), platelet-derived growth factor (PDGF), and vascular endothelial growth factor (VEGF). Examples of TKIs include, but are not limited to, afatinib, bosutinib, brigatinib, cabozantinib, crenolanib, dacomitinib, dasatinib, dovitinib, E-6201, erlotinib, gefitinib, gilteritinib (ASP-2215), HM61713, icotinib, imatinib, KX2-391 (Src), lapatinib, lestaurtinib, midostaurin, nintedanib, osimertinib (AZD-9291), ponatinib, poziotinib, quizartinib, radotinib, rociletinib, sunitinib, and TH-4000. Further anticancer agents include: alkylating agents such as thiotepa and cyclophosphamide (CYTOXAN); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, especially bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlomaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel) (TAXOL), abraxane, docetaxel) (TAXOTERE), cabazitaxel, BIND-014; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-tricUorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine) (GEMZAR®); 6-thioguanine; mercaptopurine; methotrexate; vinblastine; platinum; etoposide (VP-16); ifosfamide; mitroxantrone; vancristine; vinorelbine) (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; FOLFIRI (fluorouracil, leucovorin, and irinotecan); and pharmaceutically acceptable salts, acids, or derivatives of any of the above.

Also included in the definition of anticancer agents are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors. Examples of anti-estrogens and SERMs include, for example, tamoxifen (including NOLVADEX), raloxifene, droloxifene, 4-hydroxytamoxifen, trioxifene, keoxifene, LY117018, onapristone, and toremifene) (FARESTON). Inhibitors of the enzyme aromatase regulate estrogen production in the adrenal glands. Examples include 4(5)-imidazoles, aminoglutethimide, megestrol acetate) (MEGACE), exemestane, formestane, fadrozole, vorozole) (RIVISOR), letrozole) (FEMARA), and anastrozole) (ARIMIDEX). Examples of anti-androgens include apalutamide, abiraterone, enzalutamide, flutamide, galeterone, nilutamide, bicalutamide, leuprolide, goserelin, ODM-201, APC-100, ODM-204. Examples of progesterone receptor antagonist include onapristone.

Anti-angiogenic agents include, but are not limited to, retinoid acid and derivatives thereof, 2-methoxyestradiol, ANGIOSTATIN, ENDOSTATIN, regorafenib, necuparanib, suramin, squalamine, tissue inhibitor of metalloproteinase-1, tissue inhibitor of metalloproteinase-2, plasminogen activator inhibitor-1, plasminogen activator inbibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cis-hydroxyproline, d,I-3,4-dehydroproline, thiaproline, .alpha., .alpha.'-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Anti-fibrotic agents include, but are not limited to, the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 2004-0248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone. Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethy)dithio)butanoic acid, p-2-amino-3-methyl-3-((2-aminoethy)dithio) butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

The API can be an immunotherapeutic agent. Immunotherapeutic agents include, and are not limited to, therapeutic antibodies suitable for treating patients. Some examples of therapeutic antibodies include simtuzumab, abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, dinutuximab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, pasudotox, narnatumab, naptumomab, necitumumab, nimotuzumab, nofetumomab, obinutuzumab, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, ramucirumab (Cyramza®) rilotumumab, rituximab, robatumumab, samalizumab, satumomab, sibrotuzumab, siltuximab, solitomab, tacatuzumab, taplitumomab, tenatumomab, teprotumumab, tigatuzumab, tositumomab, trastuzumab, ABP-980, tucotuzumab, ubilituximab, veltuzumab, vorsetuzumab, votumumab, zalutumumab, CC49, OBI-833 and 3F8. Rituximab can be used for treating indolent B-cell cancers, including marginal-zone lymphoma, WM, CLL and small lymphocytic lymphoma. A combination of Rituximab and chemotherapy agents is especially effective.

The exemplified therapeutic antibodies may be further labeled or combined with a radioisotope particle such as indium-111, yttrium-90 (90Y-clivatuzumab), or iodine-131.

The composition comprises, in place of an API or in addition thereto, a targeting moiety, such as a peptide or protein ligand or domain, covalently attached to the surface of the nanoparticles, which targeting moiety specifically or preferentially binds to a target site (such as a cell surface receptor or binding partner for the targeting moiety), such that the nanoparticle bearing such a targeting moiety will be specifically or preferentially directed to the target site in vivo. The targeting moiety bearing nanoparticle may further comprise an API that is encapsulated or embedded within the nanoparticle that can be released or otherwise effective at the target site. In fact, sialic acid can itself be a targeting moiety.

By having targeting moieties, target specific nanoparticles are able to efficiently bind to or otherwise associate with a biological entity, for example, a membrane component or cell surface receptor. Targeting of a therapeutic agent (e.g., to a particular tissue or cell type, to a specific diseased tissue but not to normal tissue, etc.) is desirable for the treatment of tissue specific diseases such as cancer (e.g., prostate cancer). For example, in contrast to systemic delivery of a cytotoxic anti-cancer agent, targeted delivery could prevent the agent from killing healthy cells. Additionally, targeted delivery would allow for the administration of a lower dose of the agent, which could reduce the undesirable side effects commonly associated with traditional chemotherapy. As discussed above, the target specificity of the nanoparticles of the invention will be maximized by optimizing the ligand density on the nanoparticle. Targeting moieties can be covalently bound to the surface of the nanoparticle. For example, targeting moieties can be covalently bound to the complexing agent (lipid or polymer).

For example, a targeting moiety can be a moiety able to bind to or otherwise associate with a biological entity, for example, a membrane component, a cell surface receptor, prostate specific membrane antigen, or the like. The term "bind" or "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to molecules, such as polynucleotides, that are able to bind to or recognize a binding partner (or a limited number of binding partners) to a substantially higher degree than to other, similar biological entities. In one set of embodiments, the targeting moiety has an affinity (as measured via a disassociation constant) of less than about 1 micromolar, at least about 10 micromolar, or at least about 100 micromolar.

In preferred embodiments, the targeting moiety of the invention is a small molecule. In certain embodiments, the term "small molecule" refers to organic compounds, whether naturally-occurring or artificially created (e.g., via chemical synthesis) that have relatively low molecular weight and that are not proteins, polypeptides, or nucleic acids. Small molecules typically have multiple carbon-carbon bonds. In certain embodiments, small molecules are less than about 2000 g/mol in size. In some embodiments, small molecules are less than about 1500 g/mol or less than about 1000 g/mol. In some embodiments, small molecules are less than about 800 g/mol or less than about 500 g/mol.

In particularly preferred embodiments, the small molecule targeting moiety targets prostate cancer tumors, and, in particular, the small molecule targeting moiety is a PSMA peptidase inhibitor. These moieties are also referred to herein as "low-molecular weight PSMA ligands." When compared with expression in normal tissues, expression of prostate specific membrane antigen (PSMA) is at least 10-fold overexpressed in malignant prostate relative to normal tissue, and the level of PSMA expression is further up-regulated as the disease progresses into metastatic phases (Silver et al. 1997, Clin. Cancer Res., 3:81), as described in US Patent Publication 2014/0235706.

In some embodiments, small molecule targeting moieties that may be used to target cells associated with prostate cancer tumors include PSMA peptidase inhibitors such as 2-PMPA, GPI5232, VA-033, phenylalkylphosphonamidates (Jackson et al., 2001, Curr. Med. Chem., 8:949; Bennett et al, 1998, J. Am. Chem. Soc., 120:12139; Jackson et al., 2001, J. Med. Chem., 44:4170; Tsulcarnoto et al, 2002, Bioorg. Med. Chem. Lett., 12:2189; Tang et al., 2003, Biochem. Biophys. Res. Commun., 307:8; Oliver et al., 2003, Bioorg. Med. Chem., 11:4455; and Maung et al., 2004, Bioorg. Med. Chem., 12:4969), and/or analogs and derivatives thereof. In some embodiments, small molecule targeting moieties that may be used to target cells associated with prostate cancer tumors include thiol and indole thiol derivatives, such as 2-MPPA and 3-(2-mercaptoethyl)-1H-indole-2-carboxylic acid derivatives (Majer et al., 2003, J. Med. Chem., 46:1989; and U.S. Patent Publication 2005/0080128). In some embodiments, small molecule targeting moieties that may be used to target cells associated with prostate cancer tumors include hydroxamate derivatives (Stoermer et al., 2003, Bioorg. Med. Chem. Lett., 13:2097). In some embodiments, small molecule targeting moieties that may be used to target cells associated with prostate cancer tumors include PBDA- and urea-based inhibitors, such as ZJ 43, ZJ 11, ZJ 17, ZJ 38 (Nan et al. 2000, J. Med. Chem., 43:772; and Kozikowski et al., 2004, J. Med. Chem., 47:1729), and/or and analogs and derivatives thereof. In some embodiments, small molecule targeting moieties that may be used to target cells associated with prostate cancer tumors include putrescine, spermine, and spermidine, androgen receptor targeting agents (ARTAs), such as those described in U.S. Pat. Nos. 7,026,500; 7,022,870; 6,998,500; 6,995,284; 6,838,484; 6,569,896; 6,492,554; and in U.S. Patent Publications 2006/0287547; 2006/0276540;

2006/0258628; 2006/0241180; 2006/0183931; 2006/0035966; 2006/0009529; 2006/0004042; 2005/0033074; 2004/0260108; 2004/0260092; 2004/0167103; 2004/0147550; 2004/0147489; 2004/0087810; 2004/0067979; 2004/0052727; 2004/0029913; 2004/0014975; 2003/0232792; 2003/0232013; 2003/0225040; 2003/0162761; 2004/0087810; 2003/0022868; 2002/0173495; 2002/0099096; 2002/0099036. A related aspect of the invention provides a pharmaceutical composition comprising the subject composition, and a pharmaceutically accepted carrier or excipient. Pharmaceutical compositions are described below in more details in a separate section.

Production of the Particles

The particles can be manufactured from the coprecipitation of the polysialic acid (e.g., PSA) and a cationic lipid or polymer. In general, the polysialic acid can be dissolved in an aqueous medium or water. The cationic lipid or polymer can be dissolved in a preferably water-miscible organic solvent, such as ethanol. Any API can be dissolved in the aqueous medium or organic solvent. The two solutions are then combined. Preferably, the mixtures are combined slowly (e.g., dropwise) or with mixing (e.g., homogenization) to incur nanoprecipitation. For example, a small amount of organic solution can be added to the aqueous phase with mixing.

The particles may also be manufactured using an automated, microfluidic device such as NanoAssemblr of Precision Nanosystems and Automated Nanoparticle System of Dolomite Microfluidics.

For example, the cationic complexing agent can be dissolved in a solvent or aqueous buffer or solution. In the case an organic solvent is used, the solvent is preferably a water-miscible solvent. Examples of water-miscible solvents include acetone, methanol, ethanol, isopropanol, tetrahydrofuran, acetonitrile, dimethyl sulfoxide (DMSO), and dimethylformamide (DMF).

The SA-containing agent can be dissolved in a solvent or aqueous buffer or solution. In the case an organic solvent is used, the solvent is preferably a water-miscible solvent. Examples of water-miscible solvents include acetone, methanol, ethanol, isopropanol, tetrahydrofuran, acetonitrile, dimethyl sulfoxide (DMSO), and dimethylformamide (DMF).

The relative amount of the SA-containing agent to that of the cationic complexing agent used in the pharmaceutical composition is from 10:1 to 1:100, more preferably from 1:1 to 1:10.

As used herein, "small (amount)" refers to a relatively small amount/volume of one solution as compared to the volume of the other solution with the cationic lipid, such that an emulsion is initially formed. Typically, the volume ratio between the small amount of the organic solution and the aqueous phase, is at least about 1:n, wherein n can be 1, 2, 3, 4, 5, 6, 7, 8, 9, 10, 20, 30, 40, 50, 60, 70, 80, 90, or 100.

Using the methods of preparation described herein, the polysialic acid is tightly integrated into the produced nanoparticles.

As used herein, miscibility is defined to be the property of liquids to mix in all proportions, forming a homogeneous solution. Substances/liquids are said to be immiscible or not miscible, if in some proportion, they do not form a solution.

Exemplary solvents miscible with water include ethanol, acetone, tetrahydrofuran (THF), acetonitrile, dimethyl sulfoxide (DMSO), dimethylformamide (DMF).

Solvent is then removed and/or particles collected, for example, by evaporation, solvent exchange, centrifugation or filtration, followed by dehydration, e.g., lyophilization.

Preferably, the aqueous solution comprises a surfactant comprising organic or inorganic pharmaceutical excipients; various polymers; oligomers; natural products; nonionic, cationic, zwitterionic, or ionic surfactants; and mixtures thereof. The surfactant may comprise polyvinyl alcohol (PVA), polyvinylpyrrolidone (PVP), a polysorbate (Tween series) surfactant, a PEO-PPO-PEO (polyethylene oxide-polypropylene oxide-polyethylene oxide) triblock copolymer (Pluronic series or Poloxamer series) surfactant, or a t-octylphenyl-polyethylene glycol (Triton X-100) surfactant or a salt, derivative, copolymer, or mixture thereof.

The removal of solvent is usually achieved by, for example, solvent exchange, evaporation, and tangential flow filtration.

Combinations of more than one surfactant can be used in the invention. Useful surfactants or surface stabilizers which can be employed in the invention may include, but are not limited to, known organic and inorganic pharmaceutical excipients. Such excipients include various polymers, low molecular weight oligomers, natural products, and surfactants. Surfactants or surface stabilizers include nonionic, cationic, zwitterionic, and ionic surfactants.

Representative examples of other useful surfactants or surface stabilizers include hydroxypropyl methylcellulose, hydroxypropylcellulose, polyvinylpyrrolidone, sodium lauryl sulfate, sodium dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available TWEENS® such as e.g., TWEEN 20® and TWEEN 80® (ICI Specialty Chemicals)); polyethylene glycols (e.g., CARBOWAXS 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hydroxypropylmethylcellulose phthalate, noncrystalline cellulose, magnesium aluminum silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., PLURONICS F68® and F108®, which are block copolymers of ethylene oxide and propylene oxide); poloxamines (e.g., TETRONIC 908®, also known as POLOXAMINE 908®, which is a tetrafunctional block copolymer derived from sequential addition of propylene oxide and ethylene oxide to ethylenediamine (BASF Wyandotte Corporation, Parsippany, N.J.)); TETRONIC 1508® (T-1508) (BASF Wyandotte Corporation), TRITONS X-200®, which is an alkyl aryl polyether sulfonate (Rohm and Haas); CRODESTAS F-110®, which is a mixture of sucrose stearate and sucrose distearate (Croda Inc.); p-isononylphenoxypoly-(glycidol), also known as OLIN-10G® or SURFACTANT 10-G® (Olin Chemicals, Stamford, Conn.); Crodestas SL-40(Croda, Inc.); and SA9OHCO, which is C18H37CH2 (CON(CH3)-CH2(CHOH)4(CH2OH)2 (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-derivatized phospholipid, PEG-derivatized cholesterol, PEG-derivatized cholesterol derivative, PEG-derivatized vitamin A, PEG-derivatized vitamin E, lysozyme, random copolymers of vinyl pyrrolidone and vinyl acetate, and the like.

Examples of useful cationic surfactants or surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), polyvinylpyrrolidone-2-dimethylaminoethyl methacrylate dimethyl sulfate, 1,2 Dipalmitoyl-sn-Glycero-3-Phosphoethanolamine-N-[Amino(Polyethylene Glycol)2000] (sodium salt) (also known as DPPE-PEG(2000)-Amine Na) (Avanti Polar Lipids, Alabaster, Al), Poly(2-methacryloxyethyl trimethylammonium bromide) (Polysciences, Inc., Warrington, Pa.) (also known as S1001), poloxamines such as TETRONIC 908®, also known as POLOXAMINE 908®, which is a tetrafunctional block copolymer derived from sequential addition of propylene oxide and ethylene oxide to ethylenediamine (BASF Wyandotte Corporation, Parsippany, N.J.), lysozyme, long-chain polymers such as alginic acid, carrageenan (FMC Corp.), and POLYOX (Dow, Midland, Mich.).

Other useful cationic stabilizers include, but are not limited to, cationic lipids, sulfonium, phosphonium, and quaternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, C12-15dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy) ammonium chloride or bromide, N-alkyl (C12-18)dimethylbenzyl ammonium chloride, N-alkyl (C14-18)dimethyl-benzyl ammonium chloride, N-tetradecylidmethylbenzyl ammonium chloride monohydrate, dimethyl didecyl ammonium chloride, N-alkyl and (C12-14) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl(C12-14) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, C12, C15, C17 trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUAT™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly[diallyl dimethylammonium chloride] and poly-[N-methyl vinyl pyridinium chloride]; and cationic guar.

Such exemplary cationic surfactants or surface stabilizers and other useful cationic surfactants or surface stabilizers are described in J. Cross and E. Singer, Cationic Surfactants: Analytical and Biological Evaluation (Marcel Dekker, 1994); P. and D. Rubingh (Editor), Cationic Surfactants: Physical Chemistry (Marcel Dekker, 1991); and J. Richmond, Cationic Surfactants: Organic Chemistry, (Marcel Dekker, 1990), each of which is incorporated by reference herein in its entirety.

Nonpolymeric cationic surfactants or surface stabilizers are any nonpolymeric compound, such as benzalkonium chloride, a carbonium compound, a phosphonium compound, an oxonium compound, a halonium compound, a cationic organometallic compound, a quaternary phosphorous compound, a pyridinium compound, an anilinium compound, an ammonium compound, a hydroxylammonium compound, a primary ammonium compound, a secondary ammonium compound, a tertiary ammonium compound, and quaternary ammonium compounds of the formula NR1R2R3R4(+). For compounds of the formula NR1R2R3R4(+): (i) none of R1-R4 are CH3; (ii) one of R1-R4 is $CH_3$; (iii) three of R1-R4 are CH3; (iv) all of R1-R4 are CH3; (v) two of R1-R4 are CH3, one of R1-R4 is C6H5CH2, and one of R1-R4 is an alkyl chain of seven carbon atoms or less; (vi) two of R1-R4 are CH3, one of R1-R4 is C6H5CH2, and one of R1-R4 is an alkyl chain of nineteen carbon atoms or more; (vii) two of R1-R4 are CH3 and one of R1-R4 is the group C6H5 (CH2)n, where n>1; (viii) two of R1-R4 are CH3, one of R1-R4 is C6H5CH2, and one of R1-R4 comprises at least one heteroatom; (ix) two of R1-R4 are CH3, one of R1-R4 is C6H5CH2, and one of R1-R4 comprises at least one halogen; (x) two of R1-R4 are CH3, one of R1-R4 is C6H5CH2, and one of R1-R4 comprises at least one cyclic fragment; (xi) two of R1-R4 are CH3 and one of R1-R4 is a phenyl ring; or (xii) two of R1-R4 are CH3 and two of R1-R4 are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), di stearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Most of these surfactants or surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference.

The surfactants or surface stabilizers are commercially available and/or can be prepared by techniques known in the art.

The incorporation of the polysialic acid into the particles can be stable and tight. Thus, preferably, the method further comprises washing said nanoparticles, and/or concentrating said nanoparticles to a desired volume.

The nanoparticles produced using the methods of the invention may routinely undergo washing as part of a purification process that removes impurity, and/or concentrates the nanoparticles so produced.

The nanoparticles produced using the methods of the invention may also undergo more stringent washing tests, e.g., as part of the quality control process, to ensure that the polysialic acid residues are stably incorporated into the nanoparticles so produced.

Particle Sizes

The size of the subject nanoparticles is from about 1 nm to about 10 μm, preferably from about 10 nm to about 2 μm, and more preferably from about 20 nm to about 1 μm, and most preferably from about 50 nm to about 500 nm. For example, the nanoparticles may have an average size between about 50 and 900 nm, such as about 50, 100, 300, 500, 700, or 900 nm.

As used herein, particle size can be determined by any conventional particle size measuring techniques well known to those skilled in the art. Such techniques include, for example, sedimentation field flow fractionation, photon correlation spectroscopy, light scattering, dynamic light scattering, light diffraction, and disk centrifugation.

Additional Components

The particles of the present invention may also contain additional components. For example, carriers may have imaging agents incorporated or conjugated to the carrier. An example of a carrier nanosphere having an imaging agent that is currently commercially available is the Kodak X-sight nanospheres. Inorganic quantum-confined luminescent nanocrystals, known as quantum dots (QDs), have emerged as ideal donors in FRET applications: their high quantum yield and tunable size-dependent Stokes Shifts permit different sizes to emit from blue to infrared when excited at a single ultraviolet wavelength. (Bruchez et al., *Science,* 1998, 281:2013; Niemeyer, C. M., *Angew. Chem. Int. Ed.,* 2003, 42:5796; Waggoner, A. *Methods Enzymol.,* 1995, 246:362; Brus, L. E., *J. Chem. Phys.,* 1993, 79, 5566). Quantum dots, such as hybrid organic/inorganic quantum dots based on a class of polymers known as dendrimers, may be used in biological labeling, imaging, and optical biosensing systems (Lemon et al., *J. Am. Chem. Soc.,* 2000, 122: 12886). Unlike the traditional synthesis of inorganic quantum dots, the synthesis of these hybrid quantum dot nanoparticles does not require high temperatures or highly toxic, unstable reagents. (Etienne et al., *Appl. Phys. Lett.,* 87:181913, 2005).

Exemplary Uses

The particles and compositions thereof that have numerous applications including in therapeutic methods. There are 14 known functional Siglecs in humans and they are Siglec-1 (sialoadhesin), Siglec-2 (CD22), Siglec-3 (CD33), Siglec-4 (MAG), Siglec-5, Siglec-6, Siglec-7, Siglec-8, Siglec-9, Siglec-10, Siglec-11, Siglec-14, Siglec-15 and Siglec-16. The cytoplasmic domain of most of these Siglecs have immune receptor tyrosine-based inhibitory motifs (ITIMs) and signal negatively via recruitment of tyrosine phosphatases such as SHP-1 and SHP-2. A few Siglecs, such as Siglec-14, Siglec-15, and Siglec-16 associate with the tyrosine-based activation motif (ITAM) adaptor DAP12 via a positively charged amino acid in their transmembrane region. These Siglecs are expressed in various immune cells and have different functionalities. In general, binding Siglecs having ITIMs activates certain immune responses, and binding Siglecs having ITAMs deactivates immune actions.

Therefore, one of the applications of the present invention is to use the SA-containing nanoparticles to bind Siglecs that have ITIMs to activate immune responses to pathogens such as infection and tumor thus to treat infectious disease and cancer.

Another application of the present invention is to use the SA-containing nanoparticles to bind Siglecs that have ITAMs to deactivate certain immune responses and can thus treat inflammatory and autoimmune diseases.

Additionally, a drug can be incorporated into the subject nanoparticle and be delivered into specific cells via receptor-mediated endocytosis. For example, an mRNA can be incorporated into the subject nanoparticles and be delivered to certain cells with enhanced cell targeting and transfection.

Preferably, the nanoparticles or the composition comprising the nanoparticles can be used in a method of treating a disease or condition in a subject in need thereof, or a method of reducing the duration or severity of the disease or condition in the subject in need thereof, wherein the disease or condition is treatable with the particles (and optionally with a specific API), comprising administering a composition or a pharmaceutical composition comprising the particles to the subject, thereby treating the disease or condition. Where the particles comprise an API, the particles can be used in a method of administering or delivering the API to a subject in need thereof and/or for a method of treating a subject suffering from a disease or condition that can be treated with the API. For example, when the API is an anti-inflammatory agent, the particles can be administered to a subject from an inflammatory condition.

In additional aspects, the particles comprise an immunotherapeutic agent and can be used in immunotherapy.

The nanoparticles described herein can be used to treat an inflammatory condition. Examples of such diseases and conditions include, but are not limited to, autoimmune hemolytic anemia, idiopathic thrombocytopenic purpura, rheumatoid arthritis, celiac disease, hyper-IgM immunodeficiency, arteriosclerosis, atherosclerosis, coronary artery disease, sepsis, myocarditis, encephalitis, transplant rejection, hepatitis, thyroiditis (e.g. Hashimoto's thyroiditis, Graves disease), osteoporosis, polymyositis, dermatomyositis, Type I diabetes, Type II diabetes, gout, dermatitis, alopecia areata, systemic lupus erythematosus, Sjogren's syndrome, lichen sclerosis, scleroderma, ulcerative colitis, diabetic retinopathy, pelvic inflammatory disease, periodontal disease, arthritis, juvenile chronic arthritis (e.g. chronic iridocyclitis), psoriasis, osteoporosis, nephropathy in diabetes mellitus, asthma, pelvic inflammatory disease, chronic inflammatory liver disease, chronic inflammatory lung disease, lung fibrosis, liver fibrosis, chronic inflammatory lung disease, inflammatory bowel disease (IBD), Crohn's disease, ulcerative colitis, peritonitis, cardiovascular disease, reperfusion injury, ischemia injury, stroke, burns, and other acute and chronic inflammatory diseases of the Central Nervous System (CNS; e.g. multiple sclerosis), gastrointestinal system, the skin and associated structures, the immune system, the hepato-biliary system, or any site in the body where pathology can occur with an inflammatory component. Inflammatory diseases also include diseases involving the gastrointestinal tract and associated tissues (such as ileus, appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, coeliac disease, hepatitis, Crohn's disease, enteritis, and Whipple's disease); systemic or local inflammatory diseases and conditions (such as asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, and sarcoidosis); diseases involving the urogenital system and associated tissues (such as septic abortion, epididymitis, vaginitis, prostatitis, and urethritis); diseases involving the respiratory system and associated tissues (such as bronchitis, emphysema, rhinitis, cystic fibrosis, pneumonitis, adult respiratory distress syndrome, pneumoultramicroscopicsilicovolcanoconiosis, alvealitis, bronchiolitis, pharyngitis, pleurisy, and sinusitis); diseases arising from infection by various viruses (such as influenza, respiratory syncytial virus, HIV, hepatitis B virus, hepatitis C virus and herpes), bacteria (such as disseminated bacteremia, Dengue fever), fungi (such as candidiasis) and protozoal and multicellular parasites (such as malaria, filariasis, amebiasis, and hydatid cysts); dermatological diseases and conditions of the skin (such as burns, dermatitis, dermatomyositis, sunburn, urticaria warts, and wheals); diseases involving the cardiovascular system and associated tissues (such as stenosis, restenosis, vasulitis, angiitis, endocarditis, arteritis, atherosclerosis, thrombophlebitis, pericarditis, congestive heart failure, myocarditis, autoimmune myocarditis, myocardial ischemia, periarteritis nodosa, and rheumatic fever); diseases involving the central or peripheral nervous system and associated tissues (such as Alzheimer's disease, meningitis, encephalitis, multiple sclerosis, cerebral infarction, cerebral embolism, Guillame-Barre syndrome, neuritis, neuralgia, spinal cord injury, paralysis, and uveitis); diseases of the bones, joints, muscles and connective tissues (such as the various arthritides and arthralgias, osteomyelitis, fasciitis, Paget's disease, gout, periodontal disease, rheumatoid arthritis, and synovitis); other autoimmune and inflammatory disorders (such as myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, and Retier's syndrome); as well as various cancers, tumors and proliferative disorders (such as Hodgkins disease); and, in any case the inflammatory or immune host response to any primary disease.

Diseases that can be treated or prevented also include allergic disorders or conditions, including allergic disease, allergy, eczema, asthma, allergic rhinitis or skin hypersensitivity.

The disease to be treated or prevented can also be a viral infection, including, for example, a coronavirus infection, a hepatitis virus infection, a West Nile virus infection, a flavivirus, an influenza infection, a rhinovirus infection, a papillomavirus infection, a paramyxovirus infection, or a parainfluenza virus infection. Preferably, the viral infection infects the central nervous system of said subject. Preferably, the viral infection causes viral encephalitis or viral meningitis. In yet other aspect, the disease to be treated is a bacterial infection. Exemplary bacterial infections are *staphylococcus* infections, *streptococcus* infections, mycobacterial infections, *bacillus* infections, *Salmonella* infections, *Vibrio* infections, spirochete infections, and *Neisseria* infections. Preferred are bacteria that infect the central nervous system of the subject. Most preferred are bacteria that cause encephalitis or meningitis.

A preferred condition for use in the claimed invention is treating cancers. The cancer to be treated can include Burkitt's lymphoma, Hodgkin's lymphoma, non-Hodgkin's lymphoma (NHL), indolent non-Hodgkin's lymphoma (iNHL), refractory iNHL, multiple myeloma (MM), chronic myeloid leukemia (CIVIL), acute lymphocytic leukemia (ALL), B-cell ALL, acute myeloid leukemia (AML), chronic lymphocytic leukemia (CLL), small lymphocytic lymphoma (SLL), myelodysplastic syndrome (MDS), myeloproliferative disease (MPD), mantle cell lymphoma (MCL), follicular lymphoma (FL), Waldestrom's macroglobulinemia (WM), T-cell lymphoma, B-cell lymphoma, diffuse large B-cell lymphoma (DLBCL), or marginal zone lymphoma (MZL). In one embodiment, the cancer is minimal residual disease (MRD). In additional embodiment, the cancer is selected from Hodgkin's lymphoma, non-Hodgkin's lymphoma (NHL), indolent non-Hodgkin's lymphoma (iNHL), and refractory iNHL. In certain embodiment, the cancer is indolent non-Hodgkin's lymphoma (iNHL). In some embodiment, the cancer is refractory iNHL. In one embodiment, the cancer is chronic lymphocytic leukemia (CLL). In other embodiment, the cancer is diffuse large B-cell lymphoma (DLBCL).

In certain embodiments, the cancer is a solid tumor is selected from the group consisting of pancreatic cancer; bladder cancer; colorectal cancer; breast cancer, including metastatic breast cancer; prostate cancer, including androgen-dependent and androgen-independent prostate cancer; kidney or renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma, hepatic carcinoma, rectal cancer, penile carcinoma, vulval cancer, thyroid cancer, salivary gland carcinoma, endometrial or uterine carcinoma, hepatoma, hepatocellular cancer, liver cancer, gastric or stomach cancer including gastrointestinal cancer, cancer of the peritoneum, squamous carcinoma of the lung, gastroesophagal cancer, biliary tract cancer, gall bladder cancer, colorectal/appendiceal cancer, squamous cell cancer (e.g., epithelial squamous cell cancer).

Any of the methods of treatment provided may be used to treat cancer at various stages. By way of example, the cancer stage includes but is not limited to early, advanced, locally advanced, remission, refractory, reoccurred after remission and progressive.

Preferably, the nanoparticle of the invention can be used in combination with a second therapeutic that is effective for treating any one of the treatable conditions.

Preferably, the subject is a human patient. Preferably, the subject is a non-human mammal, such as a non-human primate, a livestock animal (horse, mule, cattle, bull, cow, sheep, goat, pig, camel, etc.), a rodent (rabbit, hamster, mouse, rat, etc.), or a pet (cat, dog).

Preferably, the method includes administering the subject composition or pharmaceutical composition comprising the subject nanoparticles by any suitable means or routes, such as orally, nasally, intravenously, intramuscularly, ocularly, transdermally, subcutaneously, intratumorally, intravesicularly, intra-articularly, intracranially, and intraperitoneally.

Preferably, about $10^2$ to about $10^{20}$ particles are provided to the individual. Preferably, between about $10^3$ to about $10^{15}$ particles are provided. Preferably, between about $10^6$ to about $10^{12}$ particles are provided. Preferably, between about $10^8$ to about $10^{10}$ particles are provided. Preferably, the preferred dose is 0.1% solids/ml. Therefore, for 500 nm particles, a preferred dose is approximately $4\times10^9$ particles, for 50 nm nanoparticles, a preferred dose is approximately $4\times10^{12}$ particles, for 3 μm beads, a preferred dose is $2\times10^7$ beads. However, a dose that is effective in treating the particular condition to be treated is encompassed by the current invention.

The effectiveness of the nanoparticles described herein against the treatable diseases and conditions can be tested using a number of efficacy tests, including suitable animal models.

Efficacy Tests

The effectiveness of the subject composition against the treatable diseases and conditions can be tested using a number of efficacy tests, including in vitro assays, in vitro and in vivo imaging, and suitable animal models.

It is important to first test the in vitro uptake of the SA-containing nanoparticles by the cells of interest, e.g., various immune cells. The test can be conducted by incubating fluorescently labeled PSA nanoparticles with immune cells of animal or human origins. The cell update can be quantitated by counting the fluorescence intensities using flow cytometry technique. A high uptake of the nanoparticles by a specific immune cell is an indication of the binding between the sialic acid moiety on the nanoparticles and the Siglec(s) on the cell.

To test the targeting capability of the nanoparticles in vivo, the nanoparticles can be labeled with a fluorophore and injected into an animal model (tumor or non-tumor) intravenously. Several hours after the injection, cell samples are to be collected in blood, spleen, or tumor (if a tumor model). These samples are analyzed similarly to the in vitro test.

As binding a specific Siglec on one type of immune cell (e.g., T cell or B cell) can lead to either stimulatory or inhibitory immune response and as a result corresponding cytokine production, experiments can be designed such that different cytokines can be detected to confirm the appropriate immune response.

Pharmaceutical Composition

One aspect of the present invention provides pharmaceutical compositions which comprise the subject nanoparticles, and optionally comprise a pharmaceutically acceptable carrier or excipient. Preferably, these compositions optionally further comprise one or more additional therapeutic agents. Alternatively, the subject particles of the current invention may be administered to a patient in need thereof in combination with the administration of one or more other therapeutic agents. For example, additional therapeutic agents for conjoint administration or inclusion in a pharmaceutical composition with a compound of this invention may be an approved anti-inflammatory agent, an immunotherapeutic agent, or a chemotherapeutic agent, or it may be any one of a number of agents undergoing approval in the Food and Drug Administration. It will also be appreciated that certain of the subject particles of present invention can exist in free form for treatment, or where appropriate, as a pharmaceutically acceptable derivative thereof.

Preferably, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention.

Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable colloids, emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the modified particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The particles can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the modified particles only, or preferentially, in a certain part of the intestinal tract, optionally, in a delayed manner. Examples of embedding compositions which can be used include polymeric substances and waxes.

It will also be appreciated that the nanoparticles and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-inflammatory agent), or they may achieve different effects (e.g., control of any adverse effects).

Preferably, the pharmaceutical compositions containing the particles of the present invention further comprise one or more additional therapeutically active ingredients (e.g., anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, anti-nausea medications and anti-sickness drugs.

The following examples are given to illustrate the present invention. It should be understood, however, that the invention is not to be limited to the specific conditions or details described in these examples.

EXAMPLES

Examples

Example 1: Preparation of PSA/DOTAP Nanoparticles

Approximately 10 mg colominic acid (Polysialic acid, PSA) sodium salt was dissolved in 0.5 mL distilled water. The resulting solution was added into a 15 mL vial. Approximately 21 mg Dioleoyl-3-trimethylammonium propane (DOTAP) chloride salt was dissolved in 4.25 mL distilled water/ethanol=1/1 (v/v) mixture. The resulting DOTAP solution was added into the PSA solution with pipette. The resulting nanoparticles showed an average size of 311.8 nm and zeta potential of −65.8 mV.

Example 2: Preparation of PSA/PEI Nanoparticles

Approximately 10 mg colominic acid (Polysialic acid, PSA) sodium salt was dissolved in 5 mL distilled water. The resulting solution was added into a 15 mL vial. Approximately 2.6 mg polyethyleneimine (PEI) was dissolved in 0.52 mL distilled water/ethanol=1/1 (v/v) mixture. The resulting PEI solution was added into the PSA solution with a pipette. The resulting nanoparticles showed an average size of 661.5 nm and a zeta potential of −29.1 mV.

Example 3: Preparation of PSA/DOTAP Nanoparticles Containing Fluorescent DiD' Oil Approximately 350 mg colominic acid (Polysialic acid, PSA) sodium salt was dissolved in 87.5 mL distilled water. The resulting solution was poured into a 150 mL beaker and kept stirring at 300 rpm. Approximately 74 mg Dioleoyl-3-trimethylammonium propane (DOTAP) chloride salt and 0.42 mg DiD' oil: DiIC18(5) oil (1, l'-Dioctadecyl-3,3,3',3'-Tetramethylindodicarbocyanine Perchlorate) were dissolved in 14.8 mL ethanol. The resulting organic solution was injected into the stirring aqueous solution with 27 G needle. The resulting suspension was magnetically stirred for 1.5 hours. The nanoparticles were collected by ultracentrifuge and re-suspended in distilled water. The nanoparticles showed an average size of 174.5 nm and zeta potential of −54.3 mV. These particles are referred to as Sigfinity™ in the figures.

Example 4: Preparation of PSA/mRNA/Lipid Nanoparticles

Approximately 100 mg of a mixture of 1,2-dioleyloxy-3-dimethylaminopropane (DODMA), 1,2-dimyristoyl-racglycero-3-methoxypolyethylene glycol-2000 (DMG-PEG), Cholesterol and 1,2-distearoyl-sn-glycero-3-phosphocholine (DSPC) at a molar ratio of 50:1.5:38.5:10 is dissolved in 14.8 mL ethanol. Approximately 5 mg of mRNA (e.g., GFP) and 50 mg colominic acid (Polysialic acid, PSA) sodium salt are dissolved in 87.5 mL distilled water. The resulting solution is transferred into a 150 mL beaker and magnetically stirred at 300 rpm. The mRNA/PSA solution is added dropwise to the stirring aqueous solution with a 27 G needle. The resulting nanoparticle suspension is stirred, washed with distill water, collected by ultracentrifuge and re-suspended in distilled water.

Example 5: Measurement of In Vitro Uptake of DiD-Loaded Nanoparticles by Isolated Balb/c Mouse PMBCs The whole blood was collected from naïve female Balb/c mice and pooled in K2-EDTA tubes. PBMCs were isolated from the whole blood using Lymphoprep™ density gradient medium. Enriched PBMCs were then adjusted to approximately $5.0\times10^5$ to $1.0\times10^6$ cells per sample in RPMI160 containing 10% FBS and plated in a sterile 96-well U-bottom polypropylene plate. Two different concentrations (10 μg/mL and 50 μg/mL) of PLGA/DiD, and Sigfinity/DiD nanoparticles were added to PBMCs in triplicate. PMBCs treated with DiD-loaded particles were then incubated at 37° C. for 1 h and 4 h in two separate plates. After incubation, PMBCs were washed to remove any nanoparticles that were not taken up by PBMCs. Washed PBMCs were stained with anti CD45, CD3, CD4, CD8, CD20, F4/80, CD49b, CD11b, Ly6-C, CD11c and viability antibodies. The immune cell phenotype and uptake of DiD-loaded nanoparticles were determined by flow cytometry. Immune cells were phenotyped as follow: T cells (CD45+/CD3+), CD4 cells (CD45+/CD3+/CD4+), CD8 cells (CD45+/CD3+/CD8+), B cells (CD45+/CD3−/CD20+), macrophages (CD45+/CD3−/F4/80+), monocytes (CD45+/CD3−/F4/80+/CD11b+/CD11c−/Ly6−C+), dendritic cells (CD45+CD3−F4/80−CD11c+) and NK cells (CD45+CD3−CD49b+). The data were analyzed using the FlowJo software.

Figure 1B:
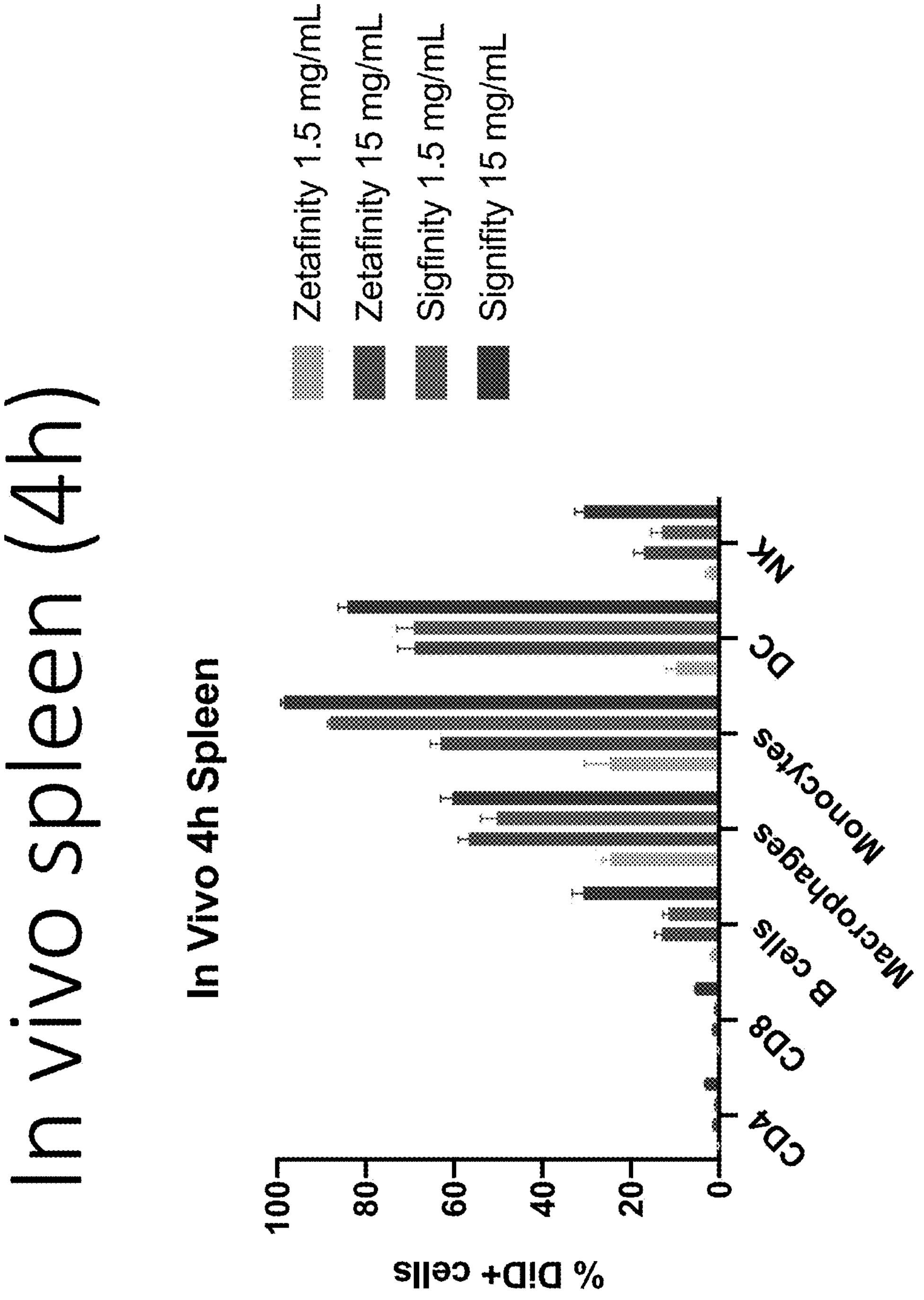
Figures 1C, 1D:
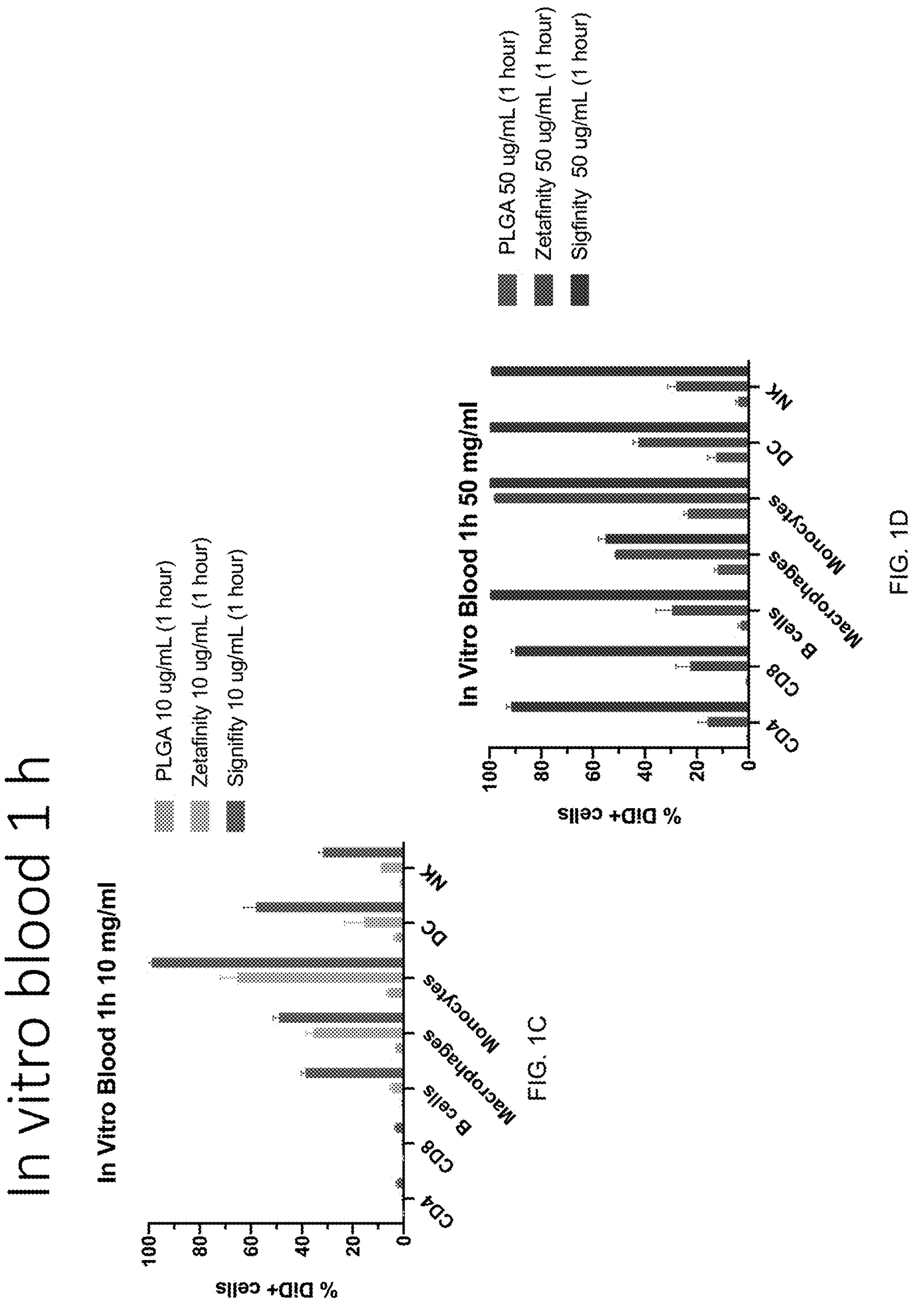
Figure 1E:
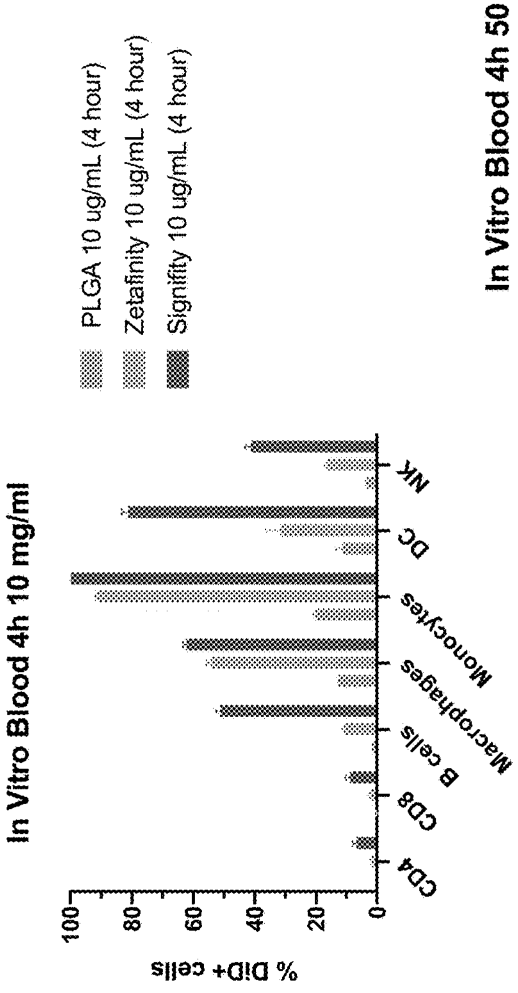
Figure 1F:
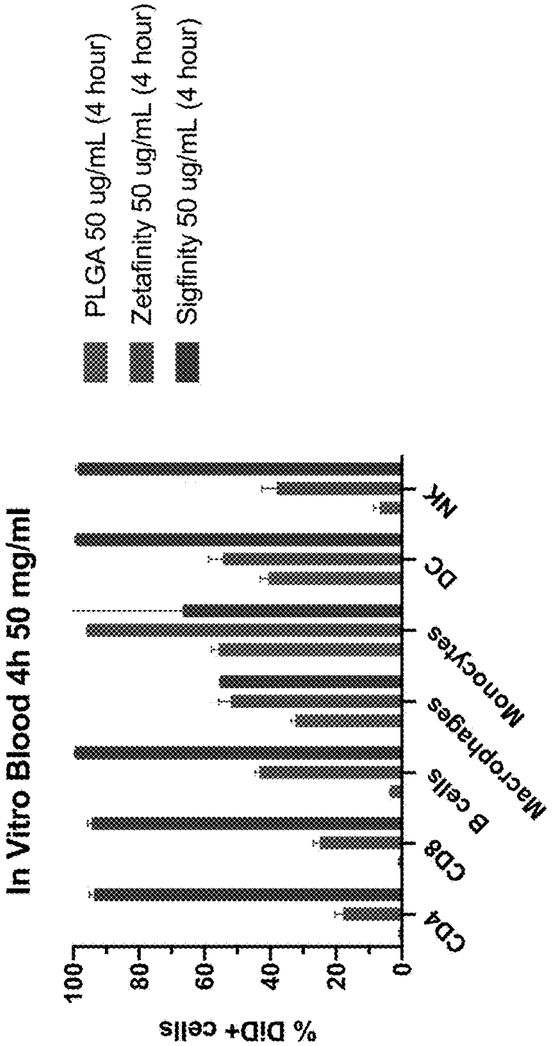
Figures 1G, 1H, 1I, 1J, 1K, 1L:
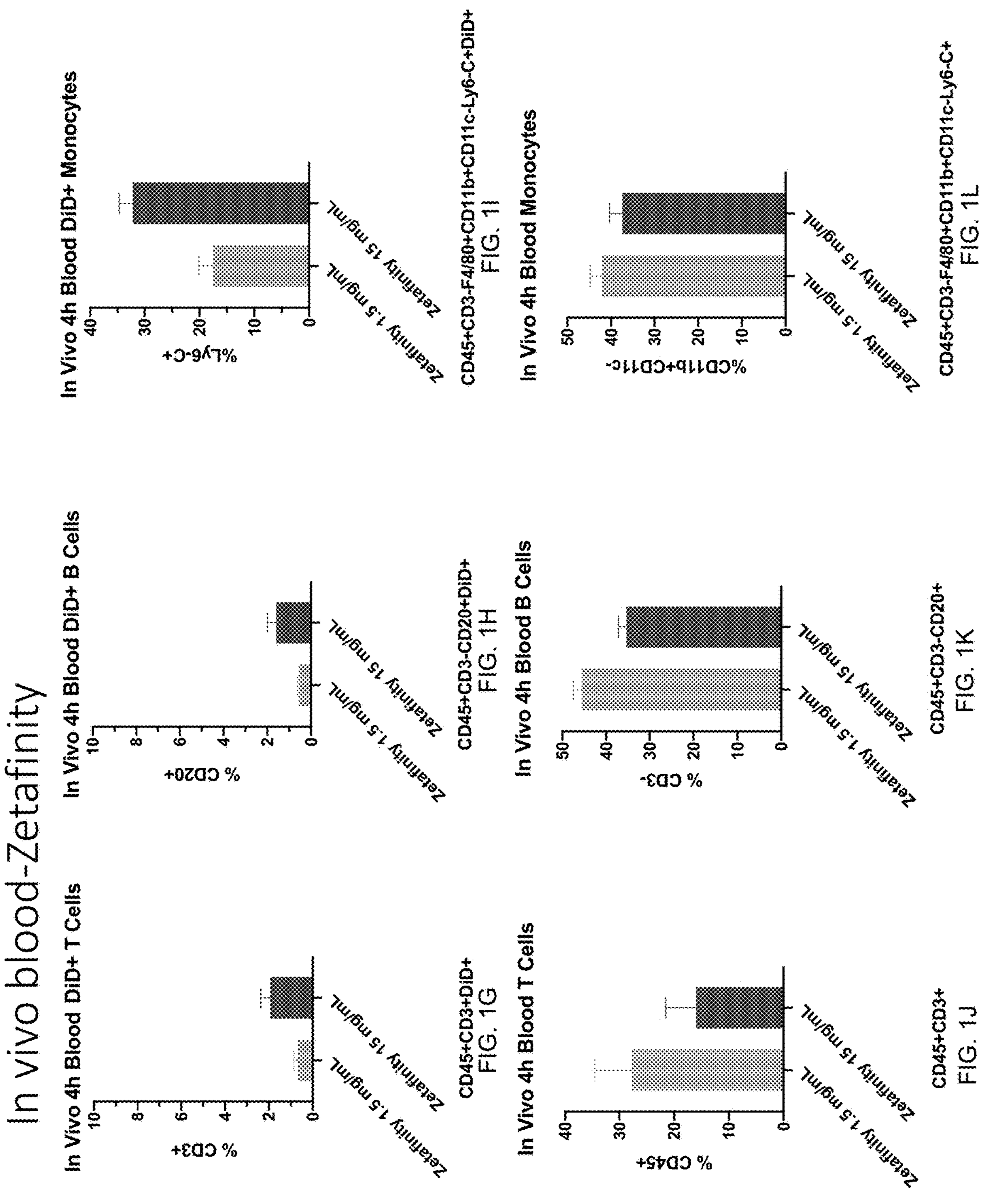
Figures 1M, 1N, 1O, 1P, 1Q, 1R:
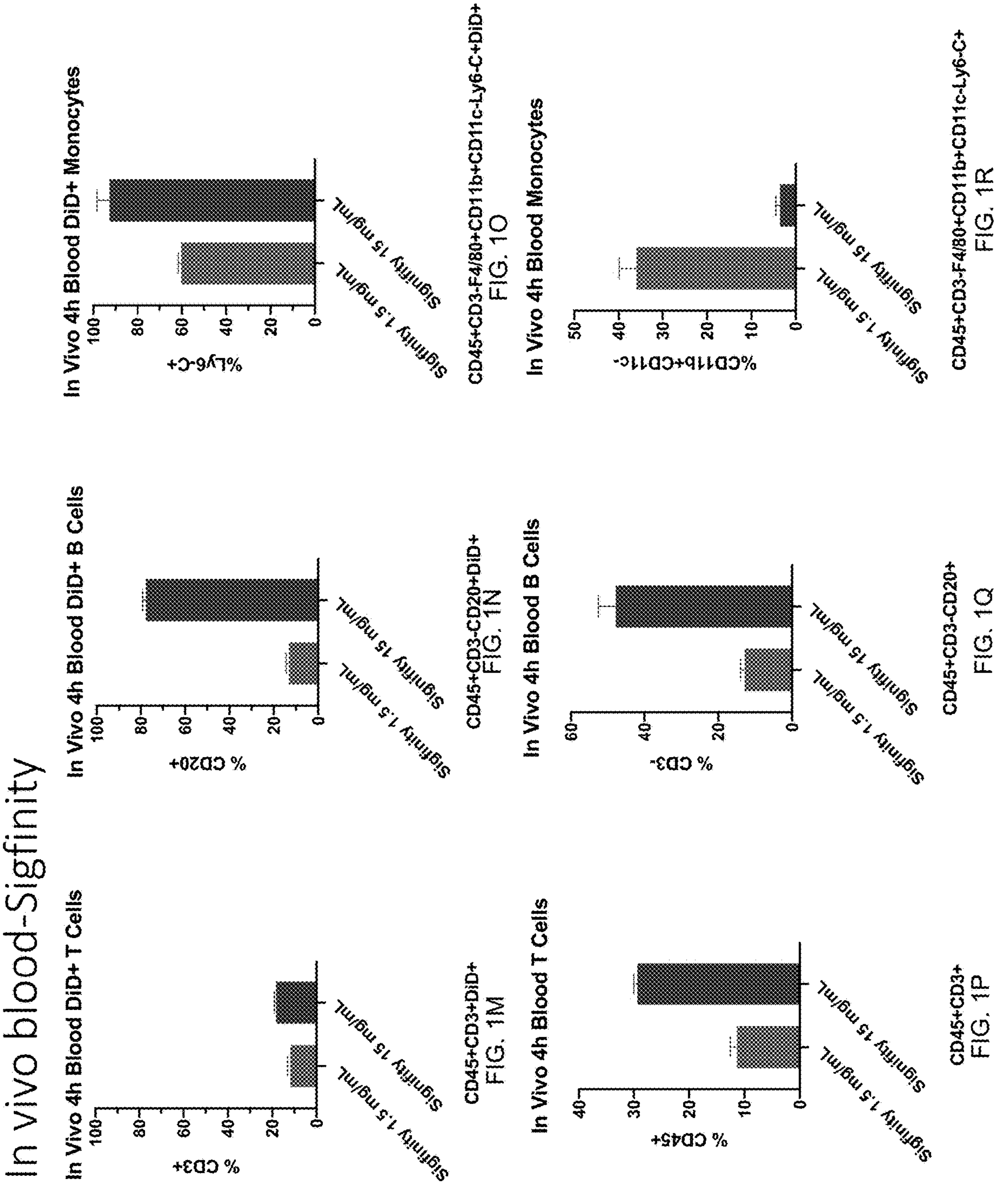
Figures 1S, 1T, 1U, 1V, 1W, 1X:
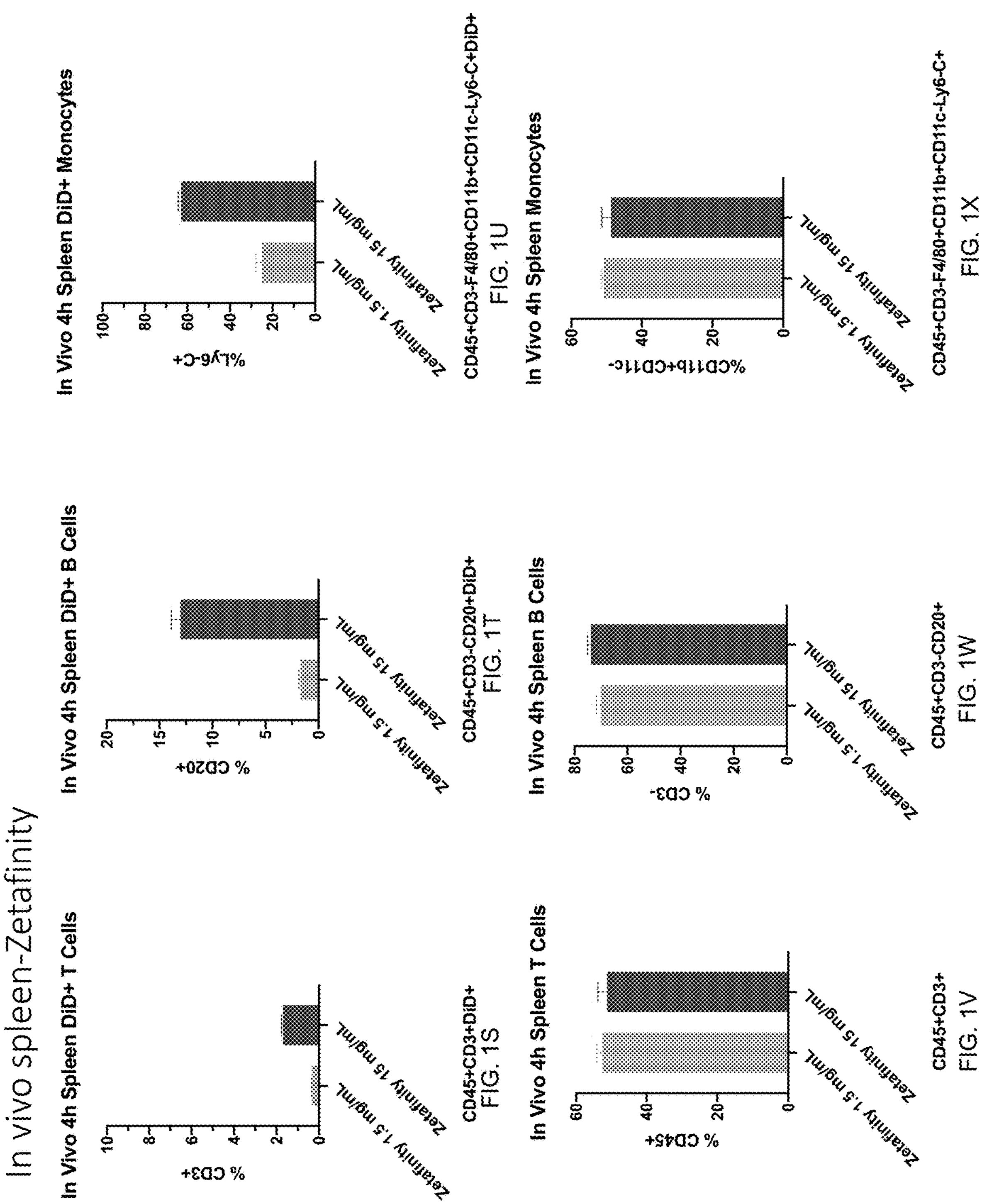
Figures 1A, 1B, 1C, 1D, 1Y, 1Z:
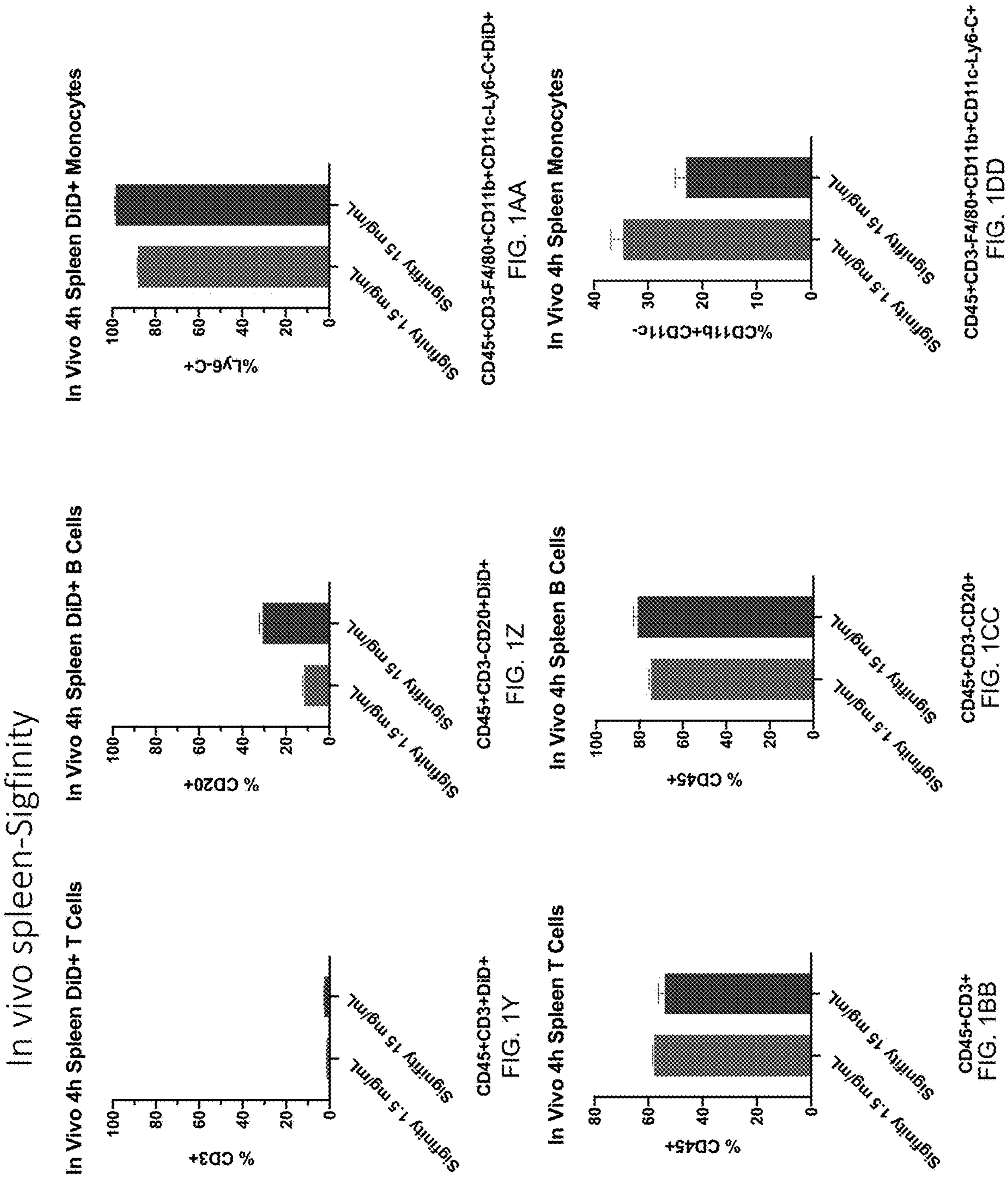
Figure 1E:
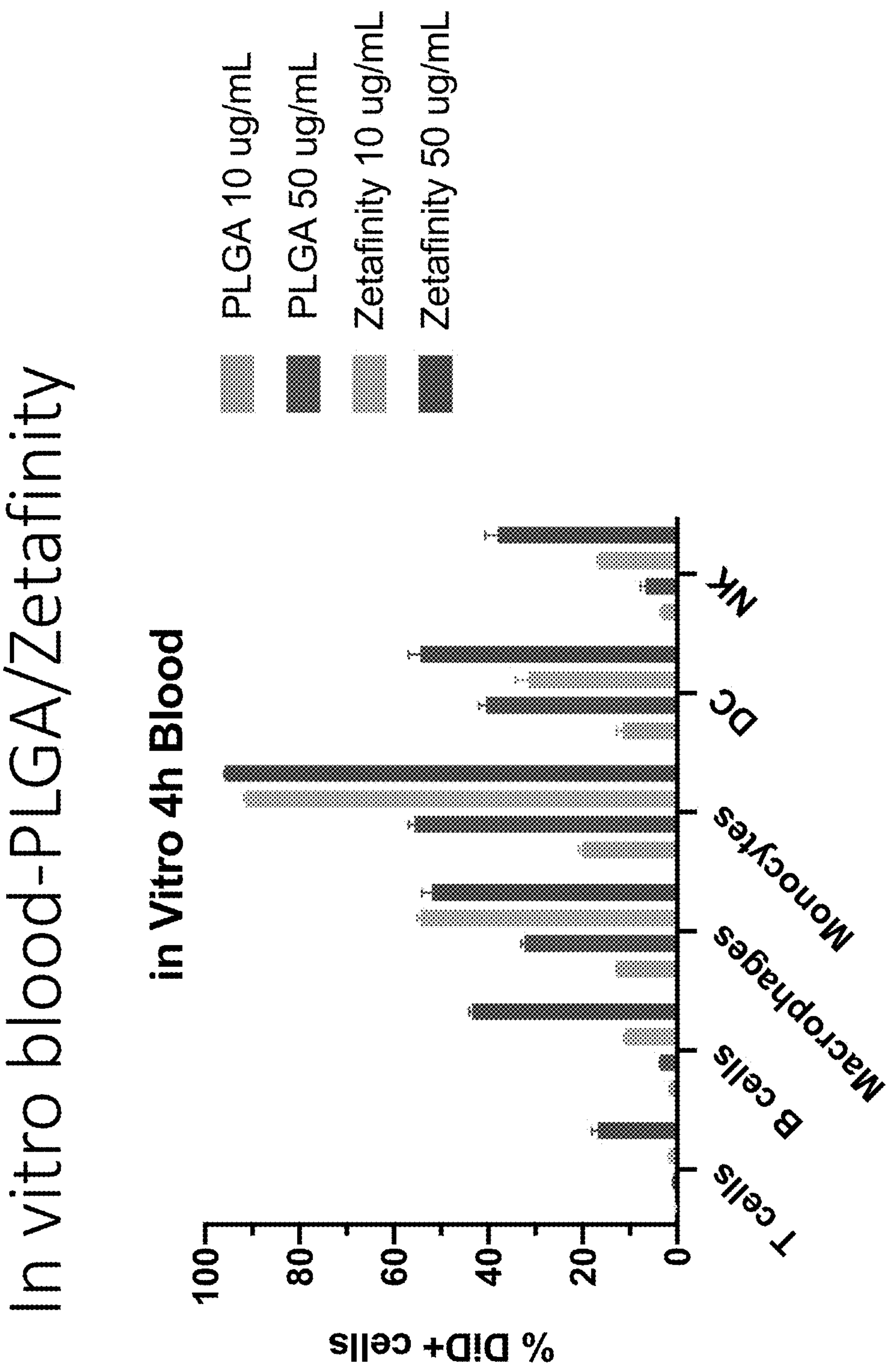
Figure 1F:
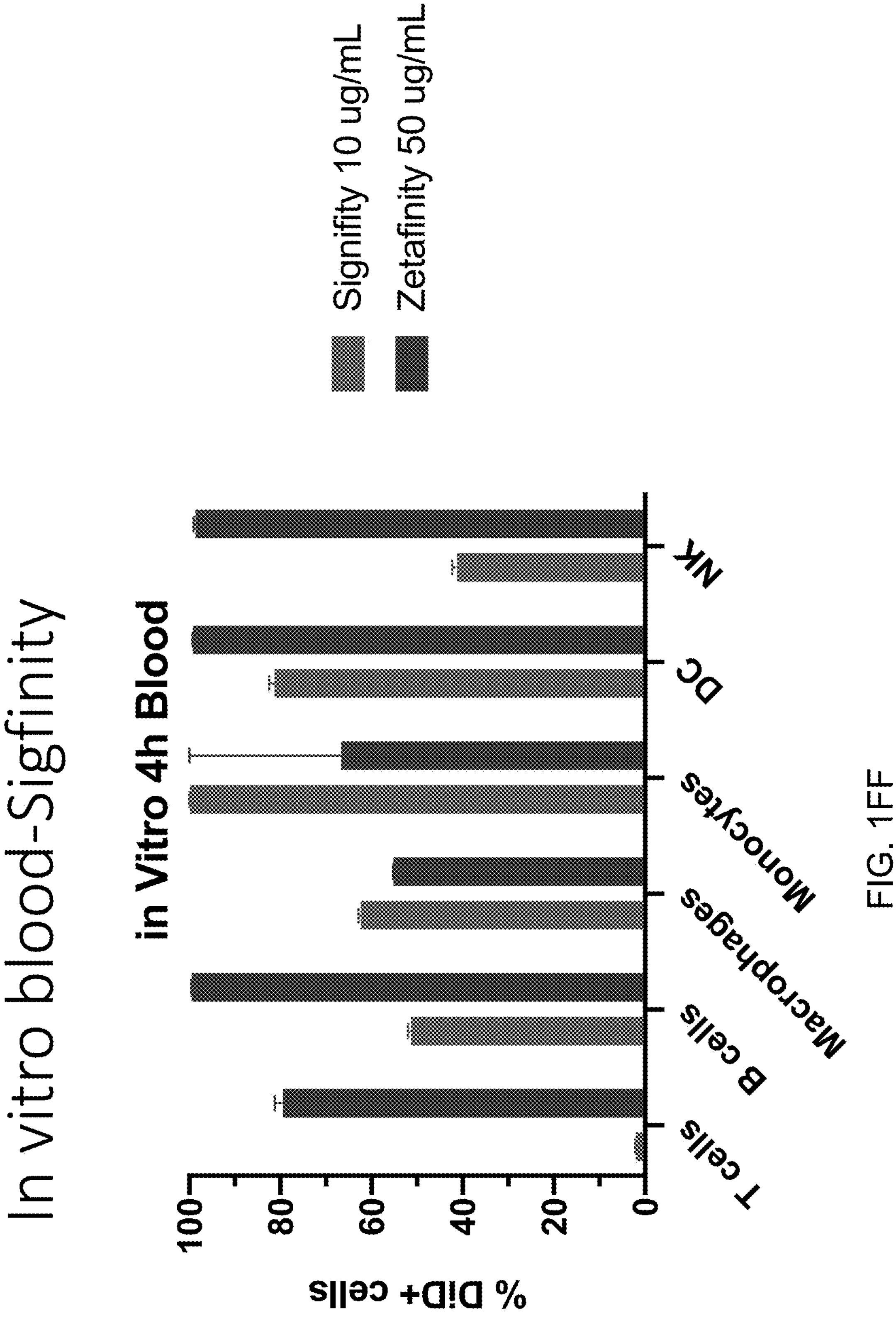
Figure 1G:
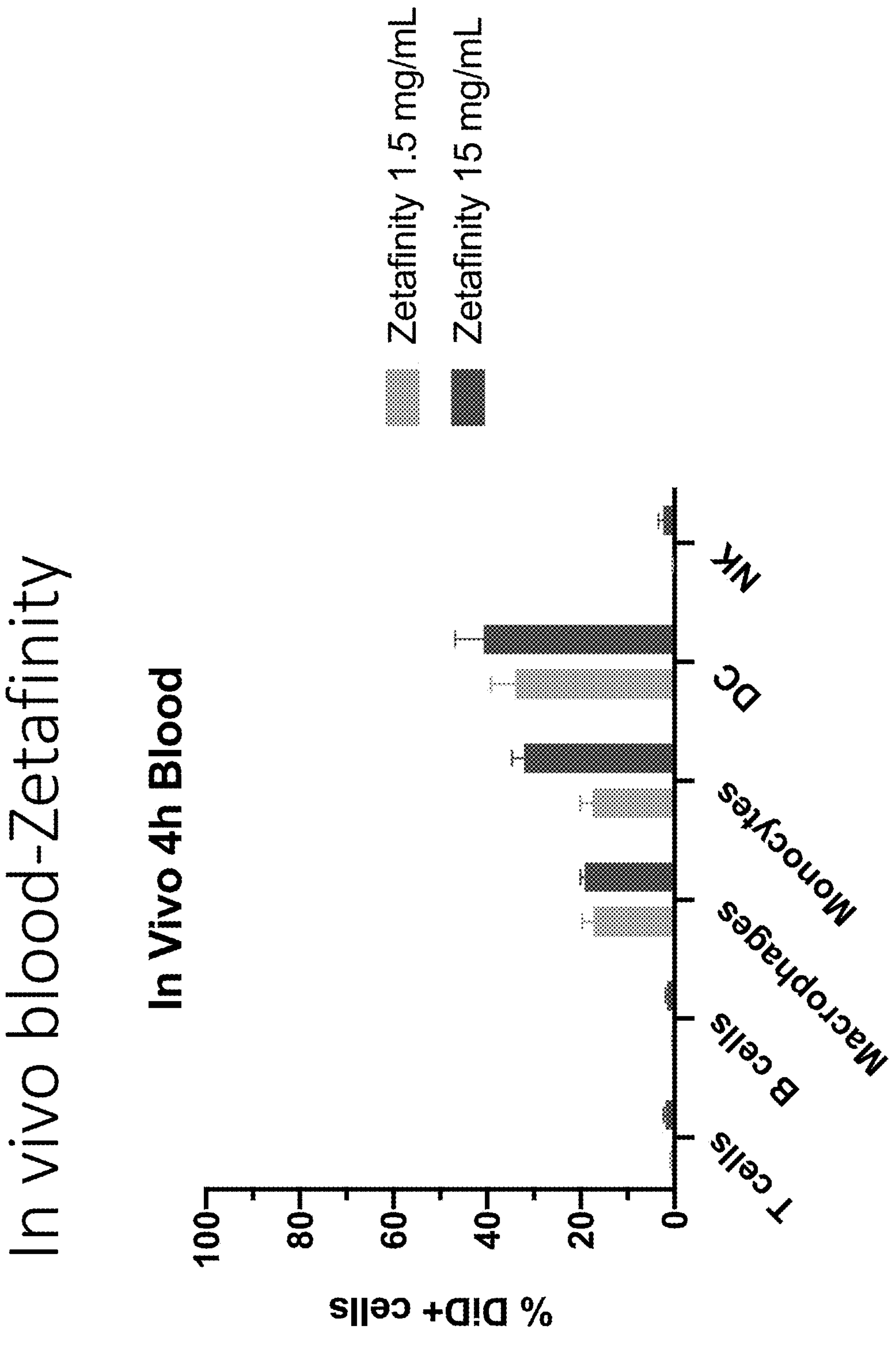
Figure 1H:
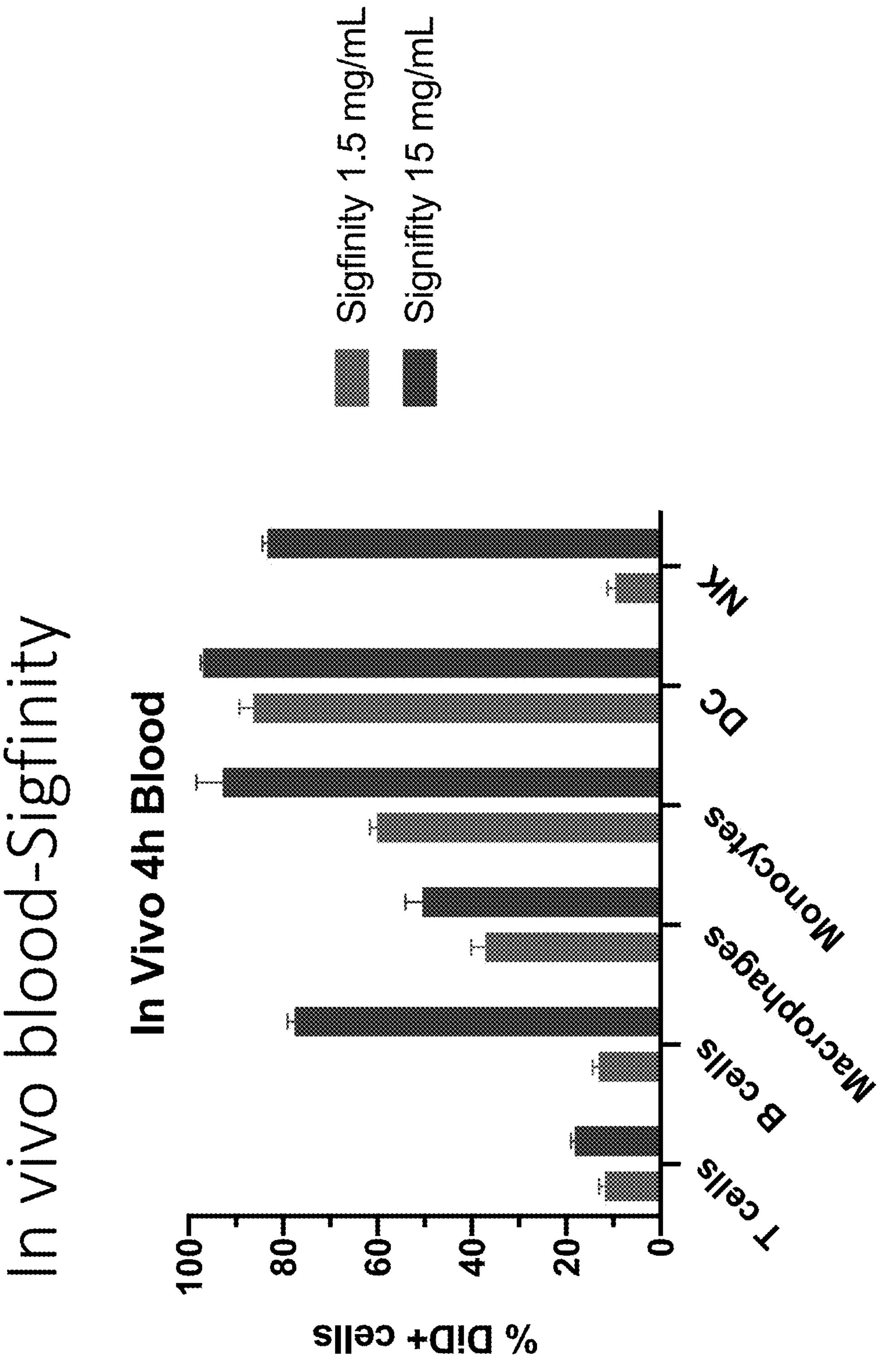
Figure 1I:
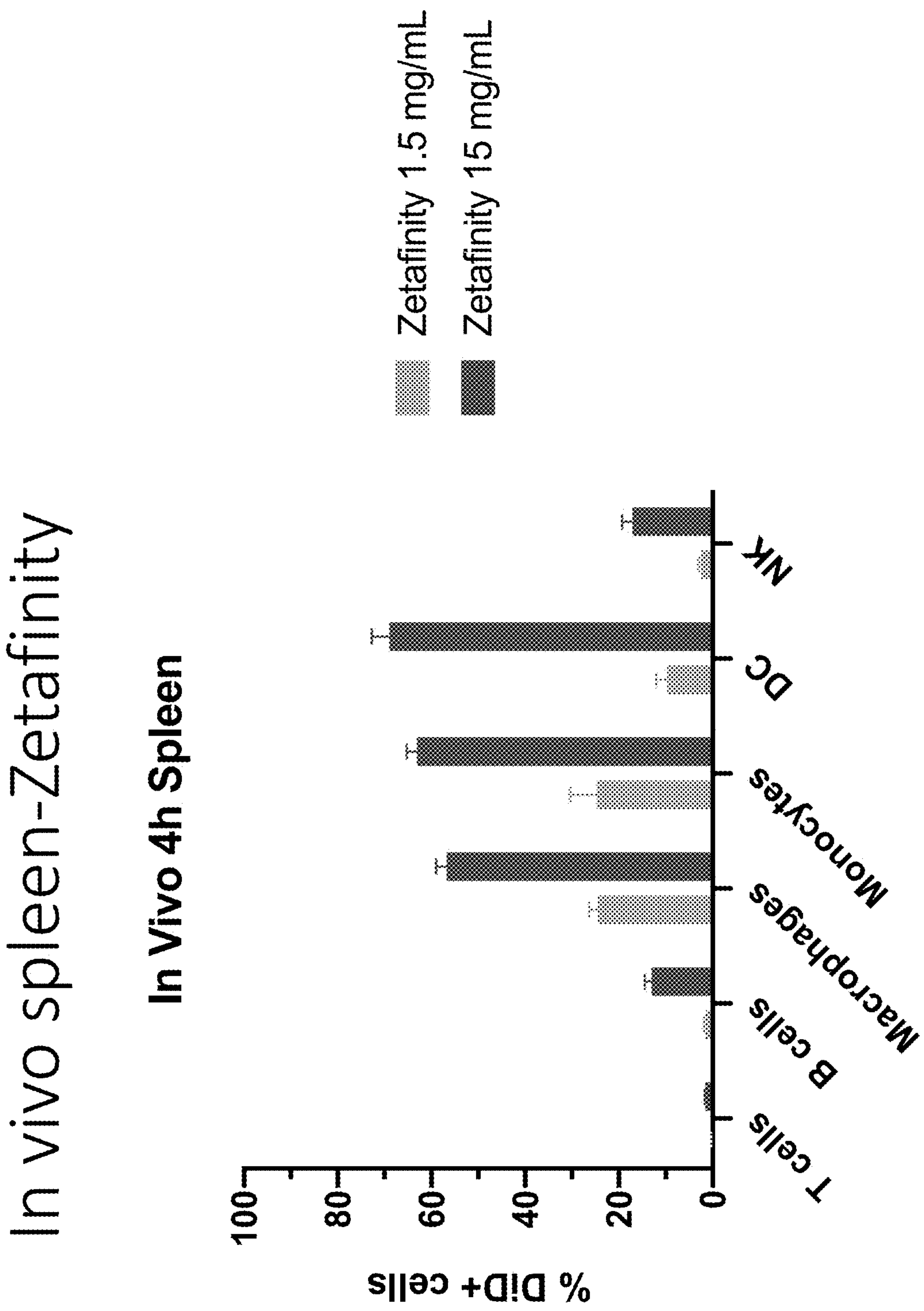
Figure 1J:
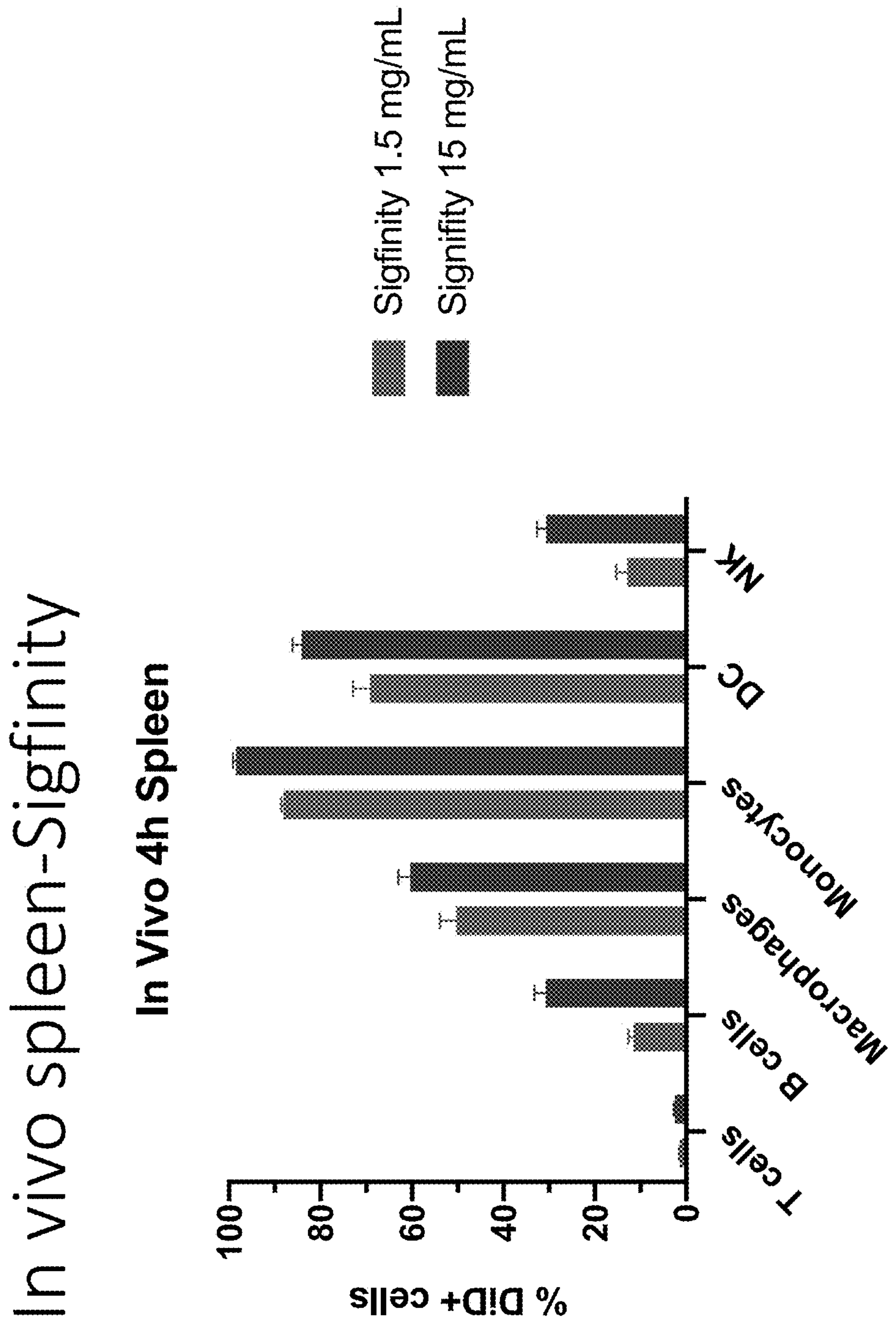

Example 6: Measurement of In Vivo Uptake of DiD-Loaded Nanoparticles by Balb/c Mouse Splenocytes and PMBCs Two different doses (15 mg/kg and 150 mg/kg) of Zetafinity®/DiD or Sigfinity™/DiD nanoparticles were administered to Balb/c female mice via the lateral tail vein in triplicate with 200 μL per mouse. At 4 h after the injection, the whole blood was collected via cardiac puncture in K2-EDTA tubes and processed for PMBCs using Lymphoprep™ density gradient medium. Spleens were also harvested and processed to single splenocytes suspension. PBMCs and splenocytes were then stained with anti CD45, CD3, CD4, CD8, CD20, F4/80, CD49b, CD11b, Ly6-C, CD11c and viability antibodies. The cell phenotype and uptake of DiD-loaded nanoparticles were determined by flow cytometry. Immune cells were phenotyped as follows: T cells (CD45+/CD3+), CD4 cells (CD45+/CD3+/CD4+), CD8 cells (CD45+/CD3+/CD8+), B cells (CD45+/CD3−/CD20+), macrophages (CD45+/CD3−/F4/80+), monocytes (CD45+/CD3−/F4/80+/CD11b+/CD11c−/Ly6−C+), dendritic cells (CD45+CD3−F4/80−CD11c+) and NK cells (CD45+CD3−CD49b+). The data were analyzed using the FlowJo software. The data is reported in FIG. 1A-1JJ.

While this invention has been particularly shown and described with references to preferred embodiments thereof, it will be understood by those skilled in the art that various changes in form and details may be made therein without departing from the scope of the invention encompassed by the appended claims.

It should be understood that any preferred features of the invention described herein can be combined with any other preferred features, including preferred features described only under one aspect of the invention, and preferred features described only in the examples. Throughout the specification, any and all references to a publicly available document, including any U.S. patent or patent application publication, are specifically incorporated by reference.

What is claimed is:

1. A composition comprising nanoparticles comprising a polysialic acid co-precipitated with a cationic lipid, and an optional active pharmaceutical ingredient, wherein the cationic lipid is Dioleoyl-3-trimethylammonium propane (DOTAP), wherein the nanoparticles have a negative zeta potential, wherein the weight ratio of the polysialic acid to DOTAP is from 10:1 to 1:2, and wherein a non-covalent complex between the polysialic acid and DOTAP is formed.

2. The composition of claim 1, wherein the polysialic acid is water soluble.

3. The composition of claim 2, wherein the polysialic acid comprises a plurality of sialic acid residues selected from the group consisting of Neu5Ac, Neu5Gc, and Kdn, or a combination thereof.

4. The composition of claim 2, wherein the polysialic acid is a homopolymer.

5. The composition of claim 2, wherein the polysialic acid is colominic acid.

6. The composition of claim 1, wherein the pharmaceutically active agent is encapsulated within the particles.

7. The composition of claim 1, wherein the nanoparticles are between about 1-1,000 nm, between about 10-1,000 nm, or between about 50-1,000 nm, or between about 100-500 nm.

8. A method for activating lymphocytes comprising contacting the lymphocytes with the composition of claim 1.

9. The method of claim 8, wherein the lymphocytes are natural killer cells.

10. A method for delivering an active pharmaceutical ingredient to cells in a subject in need thereof comprising administering to said subject the composition of claim 1.

11. The method of claim 10, wherein the cells are selected from the group consisting of T cells, B cells, macrophages, monocytes, neutrophils, dendritic cells, and natural killer cells.

12. The composition of claim 1, wherein the active pharmaceutical ingredient is present, and the amount of the active pharmaceutical ingredient is about 0.01% to about 50% (w/w) of the nanoparticle.

13. A composition comprising the nanoparticles according to claim 1, wherein the nanoparticles are prepared by a method comprising the steps of:

a. dissolving a polysialic acid and, optionally, a water soluble active pharmaceutical ingredient in an aqueous solvent to form an aqueous solution;

b. dissolving DOTAP and, optionally, a water insoluble active pharmaceutical ingredient in a water-miscible organic solvent to form an organic solution;

c. combining the aqueous solution and organic solution, thereby precipitating the nanoparticles; and d. collecting the nanoparticles.

* * * * *